United States Patent
Tsui et al.

(10) Patent No.: US 11,795,485 B2
(45) Date of Patent: Oct. 24, 2023

(54) SELECTIVE ENRICHMENT OF A POPULATION OF DNA IN A MIXED DNA SAMPLE THROUGH TARGETED SUPPRESSION OF DNA AMPLIFICATION

(71) Applicant: Day Zero Diagnostics, Inc., Allston, MA (US)

(72) Inventors: Chiahao Tsui, Somerville, MA (US); Melis Nuray Anahtar, Cambridge, MA (US); Dougal Maclaurin, Cambridge, MA (US); Miriam H. Huntley, Cambridge, MA (US); Jeffrey D. Brewster, Glenside, PA (US)

(73) Assignee: Day Zero Diagnostics, Inc., Boston, MA (US)

( * ) Notice: Subject to any disclaimer, the term of this patent is extended or adjusted under 35 U.S.C. 154(b) by 46 days.

(21) Appl. No.: 16/757,314

(22) PCT Filed: Oct. 18, 2018

(86) PCT No.: PCT/US2018/056598
§ 371 (c)(1),
(2) Date: Apr. 17, 2020

(87) PCT Pub. No.: WO2019/079656
PCT Pub. Date: Apr. 25, 2019

(65) Prior Publication Data
US 2020/0299741 A1 Sep. 24, 2020

Related U.S. Application Data

(60) Provisional application No. 62/573,720, filed on Oct. 18, 2017.

(51) Int. Cl.
| | | |
|---|---|---|
| C12N 15/11 | (2006.01) | |
| C12Q 1/68 | (2018.01) | |
| C12P 19/34 | (2006.01) | |
| C12Q 1/6806 | (2018.01) | |
| C12Q 1/689 | (2018.01) | |

(52) U.S. Cl.
CPC .............. *C12P 19/34* (2013.01); *C12N 15/11* (2013.01); *C12Q 1/6806* (2013.01); *C12Q 1/689* (2013.01)

(58) Field of Classification Search
CPC .............. C12Q 1/689; C12Q 2525/186; C12N 2310/314
See application file for complete search history.

(56) References Cited

U.S. PATENT DOCUMENTS

| | | |
|---|---|---|
| 10,544,446 B1 | 1/2020 | Tsui |
| 2003/0017591 A1 | 1/2003 | Kurn |
| 2003/0211483 A1 | 11/2003 | Schroeder et al. |
| 2004/0229271 A1 | 11/2004 | Williams |
| 2005/0118625 A1 | 6/2005 | Mounts |
| 2010/0009355 A1 | 1/2010 | Kolodney |
| 2010/0035232 A1 | 2/2010 | Ecker et al. |
| 2013/0177918 A1* | 7/2013 | Terasaki ............... C12Q 1/6858 435/6.12 |
| 2014/0017730 A1 | 1/2014 | Hicke et al. |
| 2015/0315636 A1* | 11/2015 | Nadeau ............... C12Q 1/6858 435/6.11 |
| 2015/0360193 A1* | 12/2015 | Fan ...................... B01J 19/0046 506/26 |
| 2016/0376637 A1 | 12/2016 | Ao et al. |
| 2017/0067090 A1 | 3/2017 | Zhang et al. |
| 2017/0114404 A1 | 4/2017 | Behlke et al. |

FOREIGN PATENT DOCUMENTS

| | | |
|---|---|---|
| JP | 2002-516666 A | 6/2002 |
| JP | 2005-536193 A | 12/2005 |
| JP | 2017-515484 A | 6/2017 |
| WO | WO 03/095680 A1 | 11/2003 |
| WO | WO 2014/018093 A1 | 1/2014 |
| WO | WO 2015/179339 A1 | 11/2015 |
| WO | WO 2016/187234 A1 | 11/2016 |

OTHER PUBLICATIONS

Oyola, Samuel O., et al. "Whole genome sequencing of Plasmodium falciparum from dried blood spots using selective whole genome amplification." Malaria journal 15.1 (2016): 1-12 (Year: 2016).*
Extended European Search Report for EP 18867632.4 dated Jul. 8, 2021.
International Search Report and Written Opinion for International Application No. PCT/US2018/056598 dated Jan. 24, 2019.
International Preliminary Report on Patentability for International Application No. PCT/US2018/056598 dated Apr. 30, 2020.
Boardman et al., Rapid microbial sample preparation from blood using a novel concentration device. PLoS One. Feb. 12, 2015;10(2):e0116837. doi: 10.1371/journal.pone.0116837.
Hosgood et al., Mitochondrial DNA copy number and lung cancer risk in a prospective cohort study. Carcinogenesis. May 2010;31(5):847-9. doi: 10.1093/carcin/bgq045. Epub Feb. 22, 2010.
Huang et al., Single-Cell Whole-Genome Amplification and Sequencing: Methodology and Applications. Annu Rev Genomics Hum Genet. 2015;16:79-102. doi: 10.1146/annurev-genom-090413-025352. Epub Jun. 11, 2015.
Kato et al., Loop-mediated isothermal amplification method for the rapid detection of Enterococcus faecalis in infected root canals. Oral Microbiol Immunol. Apr. 2007;22(2):131-5. doi: 10.1111/j.1399-302X.2007.00328.x.

(Continued)

*Primary Examiner* — Weihua Fan
(74) *Attorney, Agent, or Firm* — Wolf, Greenfield & Sacks, P.C.

(57) ABSTRACT

The present disclosure provides method and products for the selective enrichment of one population of DNA in a mixed sample comprising multiple populations of DNA. In some embodiments, the mixed sample comprises one or more populations of microbial DNA and the mammalian host DNA, particularly including pathogenic microbial DNA mixed with mammalian host DNA in a clinical sample from an infected individual.

20 Claims, 10 Drawing Sheets

Specification includes a Sequence Listing.

(56) References Cited

OTHER PUBLICATIONS

Kvist et al., Specific single-cell isolation and genomic amplification of uncultured microorganisms. Appl Microbiol Biotechnol. Mar. 2007;74(4):926-35. doi: 10.1007/s00253-006-0725-7. Epub Nov. 16, 2006.

Malpartida-Cardenas et al., Allele-Specific Isothermal Amplification Method Using Unmodified Self-Stabilizing Competitive Primers. Anal Chem. Oct. 16, 2018;90(20):11972-11980. doi: 10.1021/acs.analchem.8b02416. Epub Oct. 2, 2018.

Martin et al., The epidemiology of sepsis in the United States from 1979 through 2000. N Engl J Med. Apr. 17, 2003;348(16):1546-54. doi: 10.1056/NEJMoa022139.

Murgha et al., Methods for the preparation of large quantities of complex single-stranded oligonucleotide libraries. PLoS One. Apr. 14, 2014;9(4):e94752. doi: 10.1371/journal.pone.0094752.

Wu et al., Multiplexed enrichment of rare DNA variants via sequence-selective and temperature-robust amplification. Nat Biomed Eng. 2017;1:714-723. doi: 10.1038/s41551-017-0126-5. Epub Sep. 4, 2017. Erratum in: Nat Biomed Eng. Dec. 2017;1(12):1005.

EP 18867632.4, Jul. 8, 2021, Extended European Search Report.

PCT/US2018/056598, Jan. 24, 2019, International Search Report and Written Opinion.

PCT/US2018/056598, Apr. 30, 2020, International Preliminary Report on Patentability.

Jinno et al., Use of psoralen as extinguisher of contaminated DNA in PCR. Nucleic Acids Res. Nov. 25, 1990;18(22):6739. doi: 10.1093/nar/18.22.6739.

Loonen et al., Developments for improved diagnosis of bacterial bloodstream infections. Eur J Clin Microbiol Infect Dis. Oct. 2014;33(10):1687-702. doi: 10.1007/s10096-014-2153-4. Epub May 22, 2014.

Powell et al., Use of a blocking primer allows selective amplification of bacterial DNA from microalgae cultures. J Microbiol Methods. Sep. 2012;90(3):211-3. doi: 10.1016/j.mimet.2012.05.007. Epub May 17, 2012.

\* cited by examiner

| | | M13 band quantification | | E. coli band quantification | |
|---|---|---|---|---|---|
| | | Fluorescence Intensity (background subtracted) | Decrease in M13 amplification with blocker | Fluorescence Intensity (background subtracted) | Decrease in E. coli amplification with blocker |
| PCR condition | M13 primers alone | 153 | | | |
| | M13 primers + blocker | 49 | 68% | | |
| | M13 + E.coli primers alone | 127 | | 32 | |
| | M13 + E.coli primers + blocker | 73 | 43% | 28 | 13% |

FIG. 10

SEQUENCE LISTING

<160> NUMBER OF SEQ ID NOS: 79

<210> SEQ ID NO 1
<211> LENGTH: 23
<212> TYPE: DNA
<213> ORGANISM: Human

<400> SEQUENCE: 1
ccaaagttaa agatagcgga tat        23

<210> SEQ ID NO 2
<211> LENGTH: 23
<212> TYPE: DNA
<213> ORGANISM: Human

<400> SEQUENCE: 2
aattaatcat gcccttccca tat        23

```
<210> SEQ ID NO 3
<211> LENGTH: 24
<212> TYPE: DNA
<213> ORGANISM: Human

<400> SEQUENCE: 3
taaagatatt cctaataatc atat                                    24

<210> SEQ ID NO 4
<211> LENGTH: 23
<212> TYPE: DNA
<213> ORGANISM: Human

<400> SEQUENCE: 4
ccaacgccag acaatcatca tat                                     23

<210> SEQ ID NO 5
<211> LENGTH: 23
<212> TYPE: DNA
<213> ORGANISM: Human

<400> SEQUENCE: 5
aagtctcgta actggcatca tat                                     23

<210> SEQ ID NO 6
<211> LENGTH: 23
<212> TYPE: DNA
<213> ORGANISM: Human

<400> SEQUENCE: 6
cactctacca tttacgatca tat                                     23

<210> SEQ ID NO 7
<211> LENGTH: 23
<212> TYPE: DNA
<213> ORGANISM: Human

<400> SEQUENCE: 7
tcttcttaat aagctcacga tat                                     23

<210> SEQ ID NO 8
<211> LENGTH: 23
<212> TYPE: DNA
<213> ORGANISM: Human

<400> SEQUENCE: 8
aaattcccca accgatccca tat                                     23

<210> SEQ ID NO 9
<211> LENGTH: 23
<212> TYPE: DNA
<213> ORGANISM: Human

<400> SEQUENCE: 9
caccacctct tgctcagcct ata                                     23

<210> SEQ ID NO 10
<211> LENGTH: 23
<212> TYPE: DNA
<213> ORGANISM: Human

<400> SEQUENCE: 10
atagaagaac taatgttagt ata                                     23
```

```
<210> SEQ ID NO 11
<211> LENGTH: 23
<212> TYPE: DNA
<213> ORGANISM: Human

<400> SEQUENCE: 11
ctaataatcg gtgcccccga tat                                              23

<210> SEQ ID NO 12
<211> LENGTH: 23
<212> TYPE: DNA
<213> ORGANISM: Human

<400> SEQUENCE: 12
cacacattcg aagaacccgt ata                                              23

<210> SEQ ID NO 13
<211> LENGTH: 23
<212> TYPE: DNA
<213> ORGANISM: Human

<400> SEQUENCE: 13
atagggcccg tatttaccct ata                                              23

<210> SEQ ID NO 14
<211> LENGTH: 23
<212> TYPE: DNA
<213> ORGANISM: Human

<400> SEQUENCE: 14
tcacttctag gaatactagt ata                                              23

<210> SEQ ID NO 15
<211> LENGTH: 23
<212> TYPE: DNA
<213> ORGANISM: Human

<400> SEQUENCE: 15
tacctccctg acaagcgcct ata                                              23

<210> SEQ ID NO 16
<211> LENGTH: 23
<212> TYPE: DNA
<213> ORGANISM: Human

<400> SEQUENCE: 16
aatgggcctg tccttgtagt ata                                              23

<210> SEQ ID NO 17
<211> LENGTH: 23
<212> TYPE: DNA
<213> ORGANISM: Human

<400> SEQUENCE: 17
ggtttcaatt tctatcgcct ata                                              23

<210> SEQ ID NO 18
<211> LENGTH: 23
<212> TYPE: DNA
<213> ORGANISM: Human

<400> SEQUENCE: 18
ttaattagta cgggaagggt ata                                              23
```

```
<210> SEQ ID NO 19
<211> LENGTH: 24
<212> TYPE: DNA
<213> ORGANISM: Human

<400> SEQUENCE: 19
atttctataa ggattattag tata                                          24

<210> SEQ ID NO 20
<211> LENGTH: 23
<212> TYPE: DNA
<213> ORGANISM: Human

<400> SEQUENCE: 20
ggttgcggtc tgttagtagt ata                                           23

<210> SEQ ID NO 21
<211> LENGTH: 23
<212> TYPE: DNA
<213> ORGANISM: Human

<400> SEQUENCE: 21
ttcagagcat tgaccgtagt ata                                           23

<210> SEQ ID NO 22
<211> LENGTH: 23
<212> TYPE: DNA
<213> ORGANISM: Human

<400> SEQUENCE: 22
gtgagatggt aaatgctagt ata                                           23

<210> SEQ ID NO 23
<211> LENGTH: 23
<212> TYPE: DNA
<213> ORGANISM: Human

<400> SEQUENCE: 23
agaagaatta ttcgagtgct ata                                           23

<210> SEQ ID NO 24
<211> LENGTH: 23
<212> TYPE: DNA
<213> ORGANISM: Human

<400> SEQUENCE: 24
tttaaggggt tggctagggt ata                                           23

<210> SEQ ID NO 25
<211> LENGTH: 23
<212> TYPE: DNA
<213> ORGANISM: Human

<400> SEQUENCE: 25
caccacctct tgctcagcct ata                                           23

<210> SEQ ID NO 26
<211> LENGTH: 23
<212> TYPE: DNA
<213> ORGANISM: Human

<400> SEQUENCE: 26
tatactaaca ttagttcttc tat                                           23
```

```
<210> SEQ ID NO 27
<211> LENGTH: 23
<212> TYPE: DNA
<213> ORGANISM: Human

<400> SEQUENCE: 27
atatcggggg caccgattat tag                                              23

<210> SEQ ID NO 28
<211> LENGTH: 23
<212> TYPE: DNA
<213> ORGANISM: Human

<400> SEQUENCE: 28
tatacgggtt cttcgaatgt gtg                                              23

<210> SEQ ID NO 29
<211> LENGTH: 23
<212> TYPE: DNA
<213> ORGANISM: Human

<400> SEQUENCE: 29
tatagggtaa atacgggccc tat                                              23

<210> SEQ ID NO 30
<211> LENGTH: 23
<212> TYPE: DNA
<213> ORGANISM: Human

<400> SEQUENCE: 30
tatactagta ttcctagaag tga                                              23

<210> SEQ ID NO 31
<211> LENGTH: 23
<212> TYPE: DNA
<213> ORGANISM: Human

<400> SEQUENCE: 31
tataggcgct tgtcagggag gta                                              23

<210> SEQ ID NO 32
<211> LENGTH: 23
<212> TYPE: DNA
<213> ORGANISM: Human

<400> SEQUENCE: 32
tatactacaa ggacaggccc att                                              23

<210> SEQ ID NO 33
<211> LENGTH: 23
<212> TYPE: DNA
<213> ORGANISM: L. crispatus

<400> SEQUENCE: 33
taaaaagaaa taatcattaa tat                                              23

<210> SEQ ID NO 34
<211> LENGTH: 23
<212> TYPE: DNA
<213> ORGANISM: L. crispatus

<400> SEQUENCE: 34
gcgaaatatg gatatattaa tat                                              23
```

```
<210> SEQ ID NO 35
<211> LENGTH: 23
<212> TYPE: DNA
<213> ORGANISM: L. crispatus

<400> SEQUENCE: 35
gcgaaatatg gatatattaa tat                                              23

<210> SEQ ID NO 36
<211> LENGTH: 23
<212> TYPE: DNA
<213> ORGANISM: L. crispatus

<400> SEQUENCE: 36
gaagaaccac taggttcatt ata                                              23

<210> SEQ ID NO 37
<211> LENGTH: 23
<212> TYPE: DNA
<213> ORGANISM: L. crispatus

<400> SEQUENCE: 37
tcctggtaag aaaagtcatt ata                                              23

<210> SEQ ID NO 38
<211> LENGTH: 23
<212> TYPE: DNA
<213> ORGANISM: L. crispatus

<400> SEQUENCE: 38
acgagatagt aatggtaatt ata                                              23

<210> SEQ ID NO 39
<211> LENGTH: 23
<212> TYPE: DNA
<213> ORGANISM: L. crispatus

<400> SEQUENCE: 39
ggtttaatat cctaaattat ata                                              23

<210> SEQ ID NO 40
<211> LENGTH: 23
<212> TYPE: DNA
<213> ORGANISM: L. crispatus

<400> SEQUENCE: 40
ttaaaccgta cttgtaatca tat                                              23

<210> SEQ ID NO 41
<211> LENGTH: 23
<212> TYPE: DNA
<213> ORGANISM: L. crispatus

<400> SEQUENCE: 41
acatttataa taagcataat ata                                              23

<210> SEQ ID NO 42
<211> LENGTH: 23
<212> TYPE: DNA
<213> ORGANISM: L. crispatus

<400> SEQUENCE: 42
agataaaatt gactatataa tat                                              23
```

```
-continued

<210> SEQ ID NO 43
<211> LENGTH: 23
<212> TYPE: DNA
<213> ORGANISM: L. crispatus

<400> SEQUENCE: 43
agataaaatt gactatataa tat                                              23

<210> SEQ ID NO 44
<211> LENGTH: 23
<212> TYPE: DNA
<213> ORGANISM: L. crispatus

<400> SEQUENCE: 44
cctactacta ctaattaatt ata                                              23

<210> SEQ ID NO 45
<211> LENGTH: 23
<212> TYPE: DNA
<213> ORGANISM: L. crispatus

<400> SEQUENCE: 45
ggttgaaaac taatataatt ata                                              23

<210> SEQ ID NO 46
<211> LENGTH: 23
<212> TYPE: DNA
<213> ORGANISM: L. crispatus

<400> SEQUENCE: 46
caaagtgcgc tacttaatta tat                                              23

<210> SEQ ID NO 47
<211> LENGTH: 23
<212> TYPE: DNA
<213> ORGANISM: L. crispatus

<400> SEQUENCE: 47
gttgttcgcg ccaaaaccaa tat                                              23

<210> SEQ ID NO 48
<211> LENGTH: 23
<212> TYPE: DNA
<213> ORGANISM: L. crispatus

<400> SEQUENCE: 48
aaattagaaa ttgcgagtaa tat                                              23

<210> SEQ ID NO 49
<211> LENGTH: 23
<212> TYPE: DNA
<213> ORGANISM: L. crispatus

<400> SEQUENCE: 49
caagataaca cacaatactt ata                                              23

<210> SEQ ID NO 50
<211> LENGTH: 23
<212> TYPE: DNA
<213> ORGANISM: L. crispatus

<400> SEQUENCE: 50
aaaataattt aggcgtaata tat                                              23
```

```
<210> SEQ ID NO 51
<211> LENGTH: 23
<212> TYPE: DNA
<213> ORGANISM: L. crispatus

<400> SEQUENCE: 51
aaagaagcta ctaagggtaa tat                                              23

<210> SEQ ID NO 52
<211> LENGTH: 23
<212> TYPE: DNA
<213> ORGANISM: L. crispatus

<400> SEQUENCE: 52
gcgattaatg atattaataa tat                                              23

<210> SEQ ID NO 53
<211> LENGTH: 23
<212> TYPE: DNA
<213> ORGANISM: L. crispatus

<400> SEQUENCE: 53 ttcttttttgt ttctatataa tat                                             23

<210> SEQ ID NO 54
<211> LENGTH: 23
<212> TYPE: DNA
<213> ORGANISM: L. crispatus

<400> SEQUENCE: 54
gatggcaatc gtaccatcaa tat                                              23

<210> SEQ ID NO 55
<211> LENGTH: 35
<212> TYPE: DNA
<213> ORGANISM: Artificial Sequence
<220> FEATURE:
<223> OTHER INFORMATION: Synthetic

<400> SEQUENCE: 55
cgcttagcga cgttctgtcc ctctgaccac atacg                                 35

<210> SEQ ID NO 56
<211> LENGTH: 10
<212> TYPE: DNA
<213> ORGANISM: Artificial Sequence
<220> FEATURE:
<223> OTHER INFORMATION: Synthetic

<400> SEQUENCE: 56
cgtcgctaag                                                             10

<210> SEQ ID NO 57
<211> LENGTH: 32
<212> TYPE: DNA
<213> ORGANISM: Artificial Sequence
<220> FEATURE:
<223> OTHER INFORMATION: Synthetic

<400> SEQUENCE: 57
aagcaccatc taggtgtagc ctgatgccag at                                    32
```

```
<210> SEQ ID NO 58
<211> LENGTH: 13
<212> TYPE: DNA
<213> ORGANISM: Artificial Sequence
<220> FEATURE:
<223> OTHER INFORMATION: Synthetic

<400> SEQUENCE: 58
taatctggca tca                                                        13

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
cgtatgtggt cagagggaca gaa                                             23

<210> SEQ ID NO 60
<211> LENGTH: 22
<212> TYPE: DNA
<213> ORGANISM: Artificial Sequence
<220> FEATURE:
<223> OTHER INFORMATION: Synthetic

<400> SEQUENCE: 60
aagcaccatc taggtgtagc ct                                              22

<210> SEQ ID NO 61
<211> LENGTH: 32
<212> TYPE: DNA
<213> ORGANISM: Artificial Sequence
<220> FEATURE:
<223> OTHER INFORMATION: Synthetic

<400> SEQUENCE: 61
cgtctcgcct tcggactgtt agcacggcca ga                                   32

<210> SEQ ID NO 62
<211> LENGTH: 10
<212> TYPE: DNA
<213> ORGANISM: Artificial Sequence
<220> FEATURE:
<223> OTHER INFORMATION: Synthetic

<400> SEQUENCE: 62
gaaggcgaga                                                            10

<210> SEQ ID NO 63
<211> LENGTH: 12
<212> TYPE: DNA
<213> ORGANISM: Artificial Sequence
<220> FEATURE:
<223> OTHER INFORMATION: Synthetic

<400> SEQUENCE: 63
tagcatacgt gc                                                         12

<210> SEQ ID NO 64
<211> LENGTH: 31
<212> TYPE: DNA
<213> ORGANISM: Artificial Sequence
<220> FEATURE:
<223> OTHER INFORMATION: Synthetic
```

```
<400> SEQUENCE: 64
ggtgcagaga acgagacctg ggcacgtatg c                              31

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
tctggccgtg ctaacagtcc                                           20

<210> SEQ ID NO 66
<211> LENGTH: 21
<212> TYPE: DNA
<213> ORGANISM: Artificial Sequence
<220> FEATURE:
<223> OTHER INFORMATION: Synthetic

<400> SEQUENCE: 66
ggtgcagaga acgagacctg g                                         21

<210> SEQ ID NO 67
<211> LENGTH: 23
<212> TYPE: DNA
<213> ORGANISM: Artificial Sequence
<220> FEATURE:
<223> OTHER INFORMATION: Synthetic

<400> SEQUENCE: 67
gtacgtacgt acgtacgtac gta                                       23

<210> SEQ ID NO 68
<211> LENGTH: 54
<212> TYPE: DNA
<213> ORGANISM: Artificial Sequence
<220> FEATURE:
<223> OTHER INFORMATION: Synthetic

<400> SEQUENCE: 68
cgtacgtacg tacgtacgta cgtacgtacg tacgtacgta cgtacgtacg tacg     54

<210> SEQ ID NO 69
<211> LENGTH: 13
<212> TYPE: DNA
<213> ORGANISM: Artificial Sequence
<220> FEATURE:
<223> OTHER INFORMATION: Synthetic

<400> SEQUENCE: 69
cgtcgctaag cgg                                                  13

<210> SEQ ID NO 70
<211> LENGTH: 14
<212> TYPE: DNA
<213> ORGANISM: Artificial Sequence
<220> FEATURE:
<223> OTHER INFORMATION: Synthetic

<400> SEQUENCE: 70
ttaatctggc atca                                                 14
```

<210> SEQ ID NO 71
<211> LENGTH: 36
<212> TYPE: DNA
<213> ORGANISM: Artificial Sequence
<220> FEATURE:
<223> OTHER INFORMATION: Synthetic

<400> SEQUENCE: 71
ccgcttagcg acgttctgtc cctctgacca catacg                    36

<210> SEQ ID NO 72
<211> LENGTH: 35
<212> TYPE: DNA
<213> ORGANISM: Artificial Sequence
<220> FEATURE:
<223> OTHER INFORMATION: Synthetic

<400> SEQUENCE: 72
aagcaccatc taggtgtagc ctgatgccag attaa                     35

<210> SEQ ID NO 73
<211> LENGTH: 36
<212> TYPE: DNA
<213> ORGANISM: Artificial Sequence
<220> FEATURE:
<223> OTHER INFORMATION: Synthetic

<400> SEQUENCE: 73
ccgcttagcg acgttctgtc cctctgacca catacg                    36

<210> SEQ ID NO 74
<211> LENGTH: 13
<212> TYPE: DNA
<213> ORGANISM: Artificial Sequence
<220> FEATURE:
<223> OTHER INFORMATION: Synthetic

<400> SEQUENCE: 74
cgtcgctaag cgg                                             13

<210> SEQ ID NO 75
<211> LENGTH: 35
<212> TYPE: DNA
<213> ORGANISM: Artificial Sequence
<220> FEATURE:
<223> OTHER INFORMATION: Synthetic

<400> SEQUENCE: 75
aagcaccatc taggtgtagc ctgatgccag attaa                     35

<210> SEQ ID NO 76
<211> LENGTH: 14
<212> TYPE: DNA
<213> ORGANISM: Artificial Sequence
<220> FEATURE:
<223> OTHER INFORMATION: Synthetic

<400> SEQUENCE: 76
ttaatctggc atca                                            14

<210> SEQ ID NO 77
<211> LENGTH: 36
<212> TYPE: DNA
<213> ORGANISM: Artificial Sequence
<220> FEATURE:
<223> OTHER INFORMATION: Synthetic

```
<400> SEQUENCE: 77
cgtatgtggt cagagggaca gaacgtcgct aagcgg                                36

<210> SEQ ID NO 78
<211> LENGTH: 35
<212> TYPE: DNA
<213> ORGANISM: Artificial Sequence
<220> FEATURE:
<223> OTHER INFORMATION: Synthetic

<400> SEQUENCE: 78
ttaatctggc atcaggctac acctagatgg tgctt                                 35

<210> SEQ ID NO 79
<211> LENGTH: 22
<212> TYPE: DNA
<213> ORGANISM: Artificial Sequence
<220> FEATURE:
<223> OTHER INFORMATION: Synthetic

<400> SEQUENCE: 79
aagcaccatc taggtgtagc ct                                               22
```

SELECTIVE ENRICHMENT OF A POPULATION OF DNA IN A MIXED DNA SAMPLE THROUGH TARGETED SUPPRESSION OF DNA AMPLIFICATION

RELATED APPLICATIONS

This application is a national stage filing under 35 U.S.C. § 371 of international application number PCT/US2018/056598, filed Oct. 18, 2018, which was published under PCT Article 21(2) in English and claims the benefit under 35 U.S.C. § 119(e) of U.S. provisional application Ser. No. 62/573,720, filed Oct. 18, 2017, each of which is herein incorporated by reference in its entirety.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Jun. 21, 2022, is named D081970000US01-SEQ-MJT and is 12,666 bytes in size.

BACKGROUND OF INVENTION

Infections with pathogenic microbes in mammalian tissues are a major healthcare concern. Bacterial infections of the blood, known as bacteremia, can generally be treated with antibiotics, but sometimes result in sepsis, a life-threatening illness in which the entire body can become inflamed, leading to multi-organ collapse and eventual death if left untreated. The treatment of bacterial infections is becoming even more challenging with the rise of antimicrobial resistance. In the United States alone, about 2,000,000 patients a year have bacterial infections with antimicrobial resistant organisms and roughly 100,000 of those patients will die as a result of the infection. Nearly half of infections diagnosed in hospitals are now resistant to at least one common antimicrobial drug and the risk of mortality can double in cases of a drug-resistant infection. The rapid and correct identification of the pathogen(s) involved in an infection and its antimicrobial susceptibility pattern can be critical to avoiding permanent injury or death.

A major challenge to the rapid and comprehensive identification of a pathogen and its antimicrobial susceptibility pattern is that pathogens are typically a very small fraction of the biological sample. For example, in a clinically relevant sample of blood, there can be fewer than 10 pathogenic cells per milliliter of blood. At the same time, there may be billions of human cells, each of which holds approximately 1,000 times more genomic material, which presents a daunting challenge for diagnostics, particularly nucleic acid based diagnostics. The traditional method for overcoming this challenge has been to produce larger populations of the pathogen by culturing the specimen in a growth-permissive environment (e.g., a nutrient-rich broth for bacteria or fungi or a permissive cell line for viruses). Culturing pathogens can increase the pathogen:human DNA ratio by at least one million-fold but it is time consuming and can often fail to produce a successful result.

Bacterial culturing from blood, for example, can take at least 36 hours to produce a pure colony, and fails to cultivate a pathogenic microbe in almost half of severe sepsis cases (Martin et al. (2003), *New Eng. J. Med.*, 348:1546-1554). Additionally, culturing bacteria in the presence of antibiotics remains the gold standard for comprehensive antibiotic susceptibility testing (AST), but this process takes at least a few days, if not three weeks or more in the case of pathogens that are difficult to culture, such as *Mycobacterium tuberculosis*. This delay can be deadly for patients, whose risk of mortality in a severe bloodstream infection can increase 8% per hour. Rather than waiting, physicians treat using empiric therapy, which employs powerful, broad-spectrum antibiotics that are designed to "carpet bomb" the infection. This approach is expensive, exposes patients to significant drug toxicity, and encourages the spread of antibiotic resistance. Most important, empiric therapy is becoming increasingly less effective due to the risk of multi-drug resistance pathogenic microbes.

To decrease the time to diagnosis, nucleic acid based diagnostics are often employed. Current assays primarily rely on targeted nucleic acid amplification in the form of polymerase chain reaction (PCR) to selectively amplify short (<1 kilobase), pre-selected regions of the pathogen genome to detectable levels above the background human DNA levels. PCR-based diagnostics may be quick, but their reliance on targeted probes limits them to a finite number of targets, which prevents them from comprehensively identifying known pathogen species, of which there are thousands, and known antimicrobial resistance genes, of which there are at least 1,600 PCR-based diagnostics also are not always accurate in determining complex, polymorphism-based resistance. In addition, targeted amplification is blind to the genetic context of antimicrobial resistance (AMR) genes, which is crucial for cases such as polymicrobial bacterial infections, the presence of contaminants (e.g., Staphylococcal epidermidis carrying mecA), and when gene location is important.

To permit the comprehensive identification of pathogens and identify not only well-known and well-characterized resistance genes, but also more complex mechanisms of resistance, whole-genome sequencing (WGS) has emerged in the past few years as a promising new diagnostic method for both pathogen identification and antimicrobial susceptibility. Sequencing the entire genome of a pathogenic microbe after whole genome amplification (WGA) can solve some problems associated with traditional culturing. For example, using in vitro enzymatic activity to amplify DNA sequences instead of in vivo replication in a cell culture can dramatically reduce the time required to generate usable quantities of microbial genetic material from days to hours. In addition, avoiding cell culture also enables the amplification of DNA from microbes, including pathogenic microbial species, that are unculturable even with modern culture methods (e.g., Kvist et al. (2007), *Appl. Microbiol. Biotechnol.* 74(4):926-935; Huang et al. (2015), *Ann. Rev. Genomics Hum. Genet.*, 16:79-102). However, there remains a need in the art for improved methods for successfully generating whole genome sequences efficiently when host DNA or contaminating DNA can be as much as 8 to 9 logs more abundant than the DNA of interest. Selectively or preferentially amplifying and enriching a subset of nucleic acids, including pathogenic microbial DNA in a biological sample comprising a mixture of microbial and mammalian nucleic acids in an unbiased method can enable high sensitivity diagnostics using WGA.

SUMMARY OF INVENTION

The present invention depends, in part, upon the development of improved methods for enrichment of microbial nucleic acids in an amplified sample of DNA produced by amplification of a mixed sample comprising at least a first population and a second population of nucleic acids. In addition, the invention provides improved blocking oligonucleotides that can reduce the amplification of undesired sequences and, consequently, enrich the sample for desired nucleic acids when performing an untargeted amplification reaction (e.g., the use of random hexamers during isothermal amplification).

In one aspect, the invention provides improved methods for enrichment of a population of nucleic acids (e.g., microbial or non-host nucleic acids), in an amplified sample of DNA produced by amplification of a mixed sample comprising at least a first population and a second population of nucleic acids, the improvement comprising: suppressing amplification of certain sequences of in the first population of nucleic acids (e.g., mammalian or host sequences) in the mixed sample of at least a first population and a second population of nucleic acids during the step of amplification. In accordance with the invention, the amplification of certain sequences of the first population (e.g., mammalian or host DNA) is suppressed by adding to the mixed sample at least one blocking oligonucleotide which specifically binds to at least one DNA sequence in the first population of nucleic acids in the mixed sample and suppresses amplification of that bound DNA sequence. In some embodiments, sets of blocking oligonucleotides are employed which suppress amplification of a set of DNA sequences present in the first population of nucleic acids that are substantially complementary to the set of blocking oligonucleotides.

In some embodiments, the blocking oligonucleotide comprises: oligonucleotides comprising 6-23 nucleotides complementary to a sequence that occurs more frequently in a first population of nucleic acids (e.g., mammalian, mitochondrial, or host genome) than in a second population of nucleic acids (e.g., microbial, bacterial, or non-host genome). In some embodiments, the sequence occurs between 2 and 50 times more frequently in the first population of nucleic acids than in the second population of nucleic acids.

In some embodiments, the microbial genome is *Staphylococcus aureus, Staphylococcus epidermidis, Streptococcus agalactiae, Enterococcus faecalis, Enterococcus faecium, Escherichia coli, Klebsiella pneumoniae*, or any other bacterial species associated with bacteremia. In some embodiments, the at least one blocking oligonucleotide is selected from SEQ ID NOs: 1-16. In some embodiments, the at least one blocking oligonucleotide binds to a sequence selected from SEQ ID NOs: 17-32.

In some embodiments, a set of at least two blocking oligonucleotides bind to complementary sequences that are distributed across the first population of DNA (e.g., a mammalian nuclear or mitochondrial genome). In some embodiments, a set of N blocking oligonucleotides bind to complementary sequences that are distributed across the first population of DNA. Preferably, the complementary sequences are evenly distributed across the population, but this is statistically unlikely. Therefore, in some embodiments, the maximum distance between the genomic sequences complementary to the first population of blocking oligonucleotides is 2G/N, 3G/N, 4G/N or 5G/N where G is the size of the genomic DNA corresponding to the first population and N is the number of different blocking oligonucleotides in the plurality of blocking oligonucleotides.

In some embodiments, the set of blocking oligonucleotides comprises between 2 and $10^8$ different oligonucleotides. In some embodiments, the set of blocking oligonucleotides comprises between 2 and $10^3$ oligonucleotides. In some embodiments, the set of blocking oligonucleotides comprises between $10^3$ and $10^5$ oligonucleotides. In some embodiments, the set of blocking oligonucleotides comprises between $10^5$ and $10^7$ oligonucleotides. In some embodiments, the set of blocking oligonucleotides comprises between $10^7$ and $10^8$ oligonucleotides.

In some embodiments, the blocking oligonucleotide further comprises an interstrand cross-linking agent that cross-links the blocking oligonucleotide to the complementary sequence in the first population of nucleic acids (e.g., mammalian, mitochondrial, or host nucleic acids). In some embodiments, the cross-linking agent is photoactivatable. In some embodiments, the cross-linking agent is a psoralen. In some embodiments, the cross-linking agent is cisplatin, formaldehyde, nitrogen mustard, or mitomycin C.

In some embodiments, the second population of nucleic acids are microbial nucleic acids. In some embodiments, the microbial nucleic acids are bacterial, viral, fungal, or protozoal DNA.

In some embodiments, the mixed sample of a first population of nucleic acids (e.g., mammalian, mitochondrial, or host DNA) and a second population of nucleic acids (e.g., microbial, bacterial, or non-host DNA) is obtained or derived from blood, sputum, urine, mucus, saliva, tissue abscess, wound drainage, stool, lymph, lavage, cerebralspinal fluid, or any fluid aspirate or tissue extraction of human and/or other eukaryotic origin. In some embodiments, the mixed sample is obtained or derived from a human subject.

In some embodiments, the amplification is performed using a strand-displacing polymerase. In some embodiments, the amplification is by a strand-displacing polymerase selected from the group comprising: phi29 polymerase; Bst DNA polymerase, large Fragment™ (New England Biolabs, Ipswich, MA); Bsu DNA polymerase, large Fragment™ (New England Biolabs, Ipswich, MA); Deep Vent DNA Polymerase® (New England Biolabs, Ipswich, MA); Deep Vent (exo) DNA Polymerase® (New England Biolabs, Ipswich, MA); Klenow Fragment; DNA polymerase I, large fragment; M-MuLV reverse transcriptase; Therminator DNA Polymerase™ (New England Biolabs, Ipswich, MA); Vent DNA Polymerase® (New England Biolabs, Ipswich, MA); Vent (exo) DNA Polymerase® (New England Biolabs, Ipswich, MA); and SD polymerase. In some embodiments, the amplification is by phi29 polymerase.

In some embodiments, the mixed sample comprises DNA from fewer than $10^6$ microbial genomes per milliliter. In some embodiments, the mixed sample comprises DNA from fewer than microbial genomes per milliliter. In some embodiments, there is DNA from between 10 and $10^6$ microbial genomes per milliliter in the mixed sample. In some embodiments, there is DNA from between 10 and $10^3$ microbial genomes per milliliter in the mixed sample. In some embodiments, there is DNA from between $10^3$ and $10^5$ microbial genomes per milliliter in the mixed sample. In some embodiments, there is DNA from between $10^5$ and $10^6$ microbial genomes per milliliter in the mixed sample.

In some embodiments, the amplification of the second population of nucleic acids (e.g., microbial, bacterial, or non-host DNA) is increased by between 10-fold and 100-fold compared with samples not treated with the improved method.

In some embodiments, there is at least a 50% reduction in amplification of the first population of nucleic acids (e.g., mammalian, mitochondrial, or host DNA) when mixed samples are treated with the improved methods provided herein. In some embodiments, there is at least a 60%, at least 70%, at least an 80%, at least a 90%, at least a 95%, or at least a 99% reduction in the first population of nucleic acids when mixed samples are treated with the improved methods provided herein.

In some embodiments, the blocking oligonucleotide comprises a spacer at the 3' end. In some embodiments, the blocking oligonucleotide comprises 6 to 50 nucleotides.

In some aspects, the present invention provides a blocking oligonucleotide comprising: (a) at least 15 contiguous nucleotides that are complementary to a sequence that is observed more frequently within a first population of nucleic acids (e.g., mammalian, mitochondrial, or host DNA) per kilobase compared to a second population of nucleic acids (e.g., microbial, bacterial, or non-host DNA) and (b) at least one modified nucleotide that cross-links to a complementary sequence.

In some embodiments, the first population of nucleic acids is mammalian DNA. In some embodiments, the mammalian DNA is mammalian mitochondrial DNA. In some embodiments, the second population of nucleic acids is microbial DNA. In some embodiments, the microbial DNA is bacterial DNA. In some embodiments, the bacterial DNA is from *Staphylococcus aureus, Staphylococcus epidermidis, Streptococcus agalactiae, Enterococcus faecalis, Enterococcus faecium, Escherichia coli, Klebsiella pneumoniae*, or any other bacterial species associated with bacteremia. In some embodiments, the modified nucleotide is a photoactivated nucleotide. In some embodiments, the modified nucleotide is a psoralen. In some embodiments, the modified oligonucleotide is at the 3' end of the blocking oligonucleotide.

In some aspects, the present invention provides a composition comprising at least one blocking oligonucleotide that specifically binds to single-stranded DNA molecule in a first population of nucleic acids (e.g. mammalian, mitochondrial, or host) and an interstrand cross-linking agent covalently bound to the blocking oligonucleotide. In some embodiments, the blocking oligonucleotide further comprises a spacer bound to the 3' end of the blocking oligonucleotide. In some embodiments, the first population of DNA is mammalian DNA. In some embodiments, the mammalian DNA is mammalian mitochondrial DNA, optionally human mitochondrial DNA. In some embodiments, the cross-linking agent is psoralen. In some embodiments, the spacer is a C3 spacer. In some embodiments, the blocking oligonucleotide comprises between 6 to 50 nucleotides. In some embodiments, the composition comprises between 2 and $10^8$ blocking oligonucleotides.

In some aspects, the present invention provides a kit comprising the composition and a strand displacement polymerase. In some embodiments, the strand-displacing polymerase is phi29 polymerase.

In some embodiments, the second population of nucleic acids is a derived from at least one microbial genome. In some embodiments, the microbial genome is *Staphylococcus aureus, Staphylococcus epidermidis, Streptococcus agalactiae, Enterococcus faecalis, Enterococcus faecium, Escherichia coli, Klebsiella pneumoniae*, or any other bacterial species associated with bacteremia. In some embodiments, the at least one blocking oligonucleotide is selected from SEQ ID NOs: 1-16. In some embodiments, the at least one blocking oligonucleotide binds to a sequence selected from SEQ ID NOs: 17-32.

In some embodiments, a set of at least 2 blocking oligonucleotides are roughly equally distributed across the first population of nucleic acids (e.g., mammalian, mitochondrial, or host). In some embodiments, the set of blocking oligonucleotides comprises between 2 and $10^8$ oligonucleotides.

In some embodiments, the blocking oligonucleotide further comprises an interstrand cross-linking agent that cross-links the blocking oligonucleotide to a complementary sequence in the first population of DNA (e.g., mammalian, mitochondrial, or host DNA). In some embodiments, the cross-linking agent is photoactivatable. In some embodiments, the cross-linking agent is a psoralen. In some embodiments, the psoralen is at the 3' end of the oligonucleotide.

In some embodiments, the mixed sample comprises DNA from fewer than 10 microbial DNA molecules per milliliter. In some embodiments, the mixed sample comprises DNA from between 10 and $10^6$ microbial genomes per milliliter. In some embodiments, there is DNA from between 10 and $10^3$ microbial genomes per milliliter in the mixed sample. In some embodiments, there is DNA from between $10^3$ and $10^5$ microbial genomes per milliliter in the mixed sample. In some embodiments, there is DNA from between $10^5$ and $10^6$ microbial genomes per milliliter in the mixed sample.

In some embodiments, the amplification of the second population of nucleic acids (e.g., microbial, bacterial, or non-host) is increased by between 10-fold and 100-fold compared with samples not treated with the improved method.

In some embodiments, there is at least a 50% reduction in amplification of the first population of nucleic acids (e.g., mammalian, mitochondrial, or host DNA) when mixed samples are treated with the improved methods provided herein. In some embodiments, there is at least a 60%, at least 70%, at least an 80%, at least a 90%, at least a 95%, or at least a 99% reduction in the first population of nucleic acids when mixed samples are treated with the improved methods provided herein. In some embodiments, the blocking oligonucleotide comprises a spacer at the 3' end. In some embodiments, the blocking oligonucleotide comprises 6 to 50 nucleotides.

In some aspects, the present invention provides a composition comprising at least one blocking oligonucleotide that specifically binds to single-stranded DNA molecules in a first population of nucleic acids (e.g., mammalian, mitochondrial, or host DNA) and an interstrand cross-linking agent covalently bound to the blocking oligonucleotide. In some embodiments, the blocking oligonucleotide further comprises a spacer bound to the 3' end of the blocking oligonucleotide. In some embodiments, the first population of nucleic acids is mammalian DNA. In some embodiments, the mammalian DNA is human DNA. In some embodiments, the cross-linking agent is psoralen. In some embodiments, the spacer is a C3 spacer. In some embodiments, the blocking oligonucleotide comprises between 6 to 50 nucleotides. In some embodiments, the composition comprises between 2 and $10^8$ blocking oligonucleotides.

In some aspects, the present invention provides a kit comprising the composition and a strand displacement polymerase. In some embodiments, the strand-displacing polymerase is phi29 polymerase.

Stage 3: "h-adapters" are ligated to the host DNA fragments. There are two h-adapters. Adapter 1 has a 3' overhang and a sticky end that matches the X restriction site. Adapter 2 has a 5' overhang and a sticky end that matches the Y restriction site. Stage 4: the fragments with h-adapters ligated are amplified in a PCR reaction using primers that match the h-adapters. One of the primers may have a 5' phosphate group and the other primer may have a 5'biotin or a different capture group (e.g., a His tag). In this arrangement, the only fragments that are amplified are those that have an X restriction site at one end and a Y restriction site at the other end, i.e., hetero fragments. Stage 5: lambda single-strand exonuclease is used to digest (depolymerize) the phosphorylated strand, leaving single-stranded DNA fragments which we call "blocking probes" or "blocking primers". Alternative methods for obtaining single-stranded DNA may be used, such as using streptavidin to selectively pull down the biotinylated strand.

Figure 7:
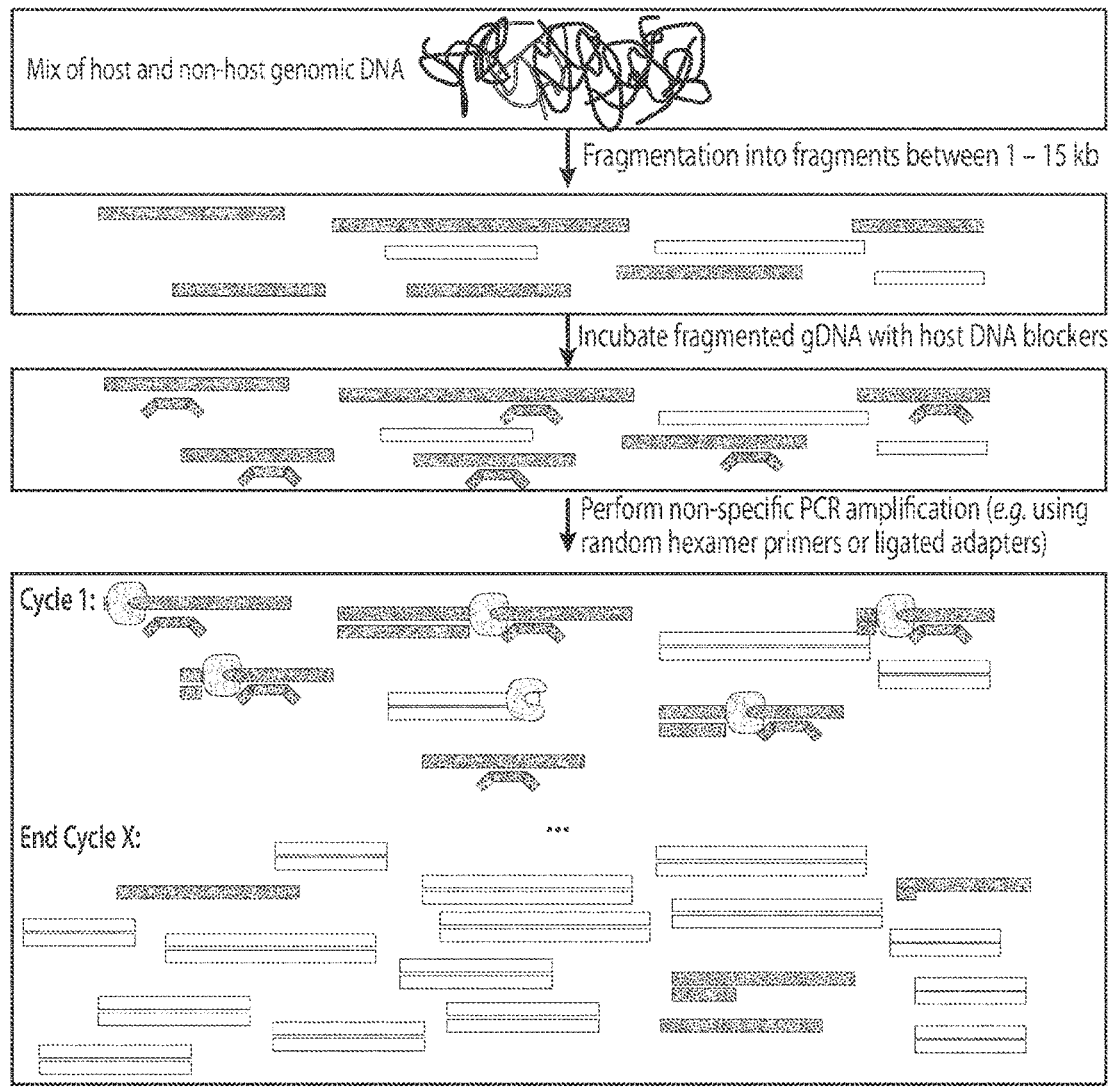

FIG. 7 shows the application of host winged DNA blockers to the amplification reaction. Stage 1: the starting sample contains a mix of host and non-host DNA. Stage 2: DNA is fragmented into fragments 1-15 kb in size. Stage 3: Fragments are incubated with the blocking probes which bind selectively to the host DNA fragments. Stage 4: non-specific PCR or other amplification is performed, using a non-strand-displacing polymerase. When the polymerase reaches the blocking fragments, it cannot process further, and thus amplification of host DNA cannot proceed. It is important that the blocking probes themselves don't act as primers. The "wings", i.e., the sequences corresponding to the 3' h-adapter, prevent extension of the blocking probes because they do not hybridize to host DNA. Because amplification of host DNA is blocked, the result is a mixture that is enriched for non-host DNA.

Figure 8:
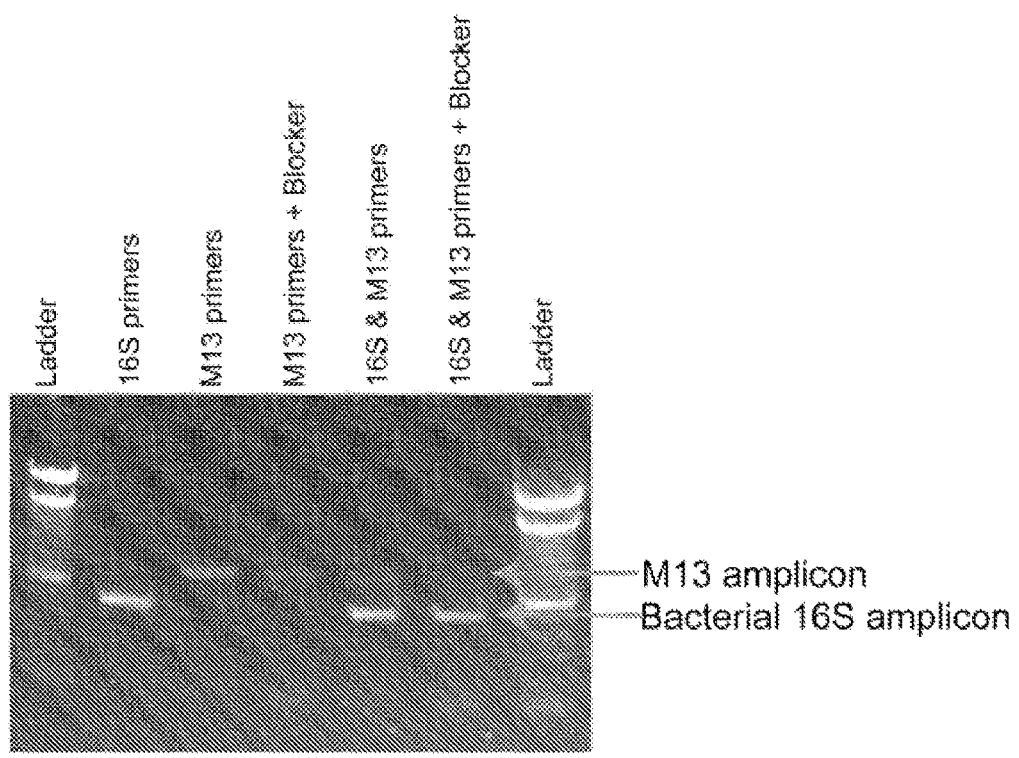

FIG. 8 shows the suppression of M13 phage amplicon amplification in the presence of *E. coli* DNA using an M13 phage blocker. In a proof of concept experiment, the amplification of a segment of the M13 phage DNA genome is blocked in the presence of *E. coli* DNA using a manufactured blocker against the M13 phage. All experimental conditions contained both *E. coli* and M13 phage DNA.

Figure 9:
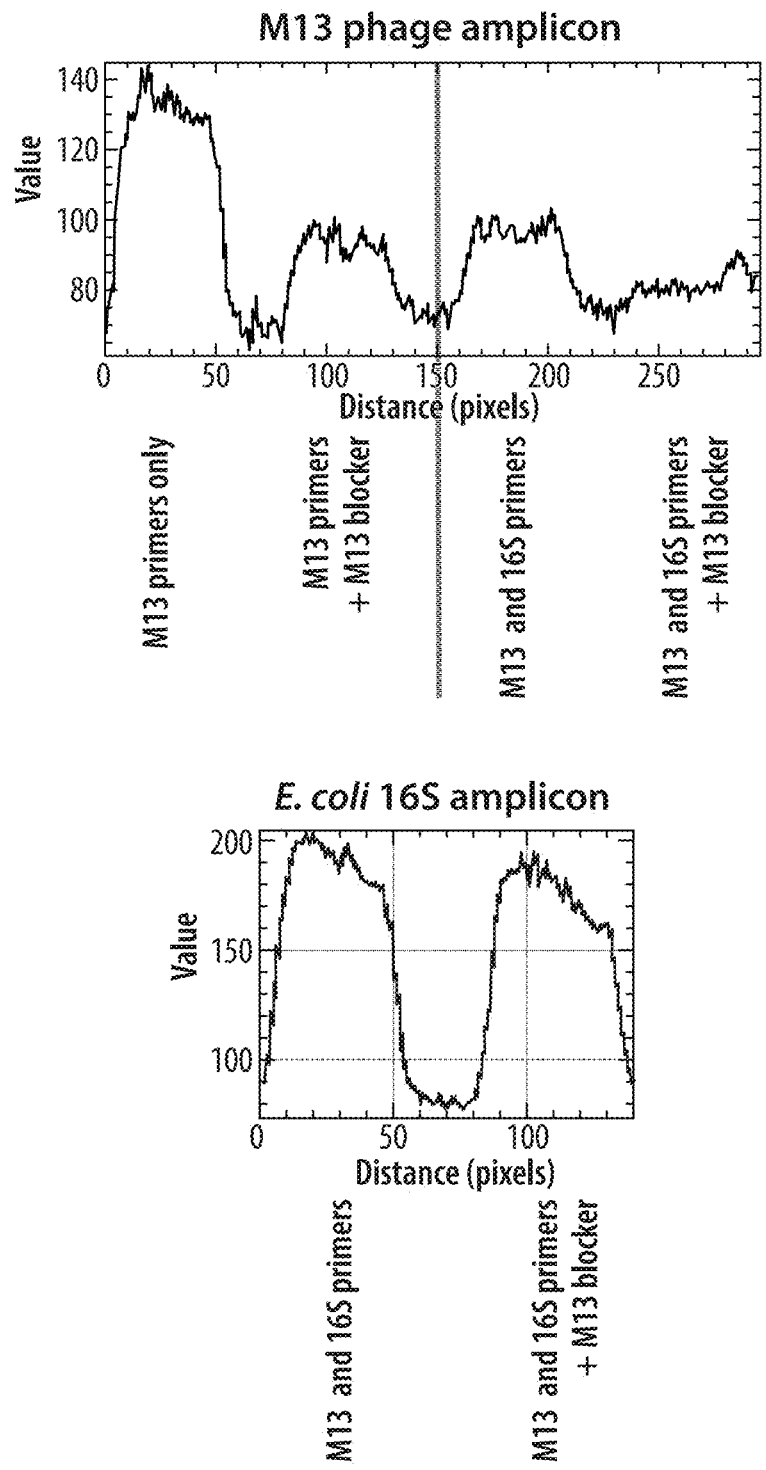

FIG. 9 shows the quantification of M13 phage amplicon suppression using an M13 blocker. The fluorescence intensity profiles from the bands illustrated in FIG. 7 are quantified using ImageJ software.

FIG. 10 shows the analysis of M13 phage amplicon suppression using an M13 blocker. The average raw fluorescent intensity across the gel bands were quantified based on the profile determined in FIG. 8. The net band fluorescent intensity was then calculated by subtracting the average background fluorescence from the average raw fluorescent intensity. The effect of the blocker was calculated by comparing the net band fluorescent intensity before and after blocker addition.

DETAILED DESCRIPTION OF INVENTION

Definitions

All scientific and technical terms used herein, unless otherwise defined below, are intended to have the same meaning as commonly understood by one of ordinary skill in the art to which this invention belongs. In the case of any conflict, the present specification, including definitions, will control. References to techniques employed herein are intended to refer to the techniques as commonly understood in the art, including variations on those techniques or substitutions of equivalent or later-developed techniques which would be apparent to one of skill in the art. In order to more clearly and concisely describe the subject matter which is the invention, the following definitions are provided for certain terms which are used in the specification and appended claims.

As used herein, the term "microbe" means a microorganism that requires a microscope to be visualized. Non-limiting examples of microbes include: bacteria, archaea, fungi, protists, viruses, and microscopic animals. Pathogenic microbes are capable of causing diseases in a host organism.

As used herein, the term "oligonucleotide" is a polymer comprising nucleotide bases. The nucleotide bases can be composed of DNA nucleotides (e.g., A, C, G, T), RNA nucleotides (e.g., A, C, G, U), or mixtures of DNA nucleotides and RNA nucleotides. The nucleotide bases may be modified (e.g., 2'-O-methyl nucleotides, peptide nucleic acids (PNAs), locked nucleic acids (LNAs), morpholinos, 2'-fluoro-deoxyribonucleotides, or bridged nucleotides such as locked nucleic acids (LNAs), or constrained ethyl nucleotides (cEts)).

As used herein the term "bacteria" means single-celled microbes of the kingdom Prokaryota.

As used herein, the term "mammal" means to a warm-blooded vertebrate eukaryote that is distinguished by the possession of hair or fur, the secretion of milk by females to nourish the young, and the birth of live young.

As used herein, "enrichment" refers to the increase of one population of DNA (e.g., microbial DNA) relative to a second population (e.g., mammalian DNA) in a mixed sample comprising at least two populations of DNA.

As used herein, "amplification" refers to the process of increasing a population of nucleic acids. The population of nucleic acids is expanded in one of several ways, including polymerase chain reaction (PCR), strand displacement amplification (SDA), or transcription mediated amplification (TMA). In some embodiments, nucleic acid amplification is isothermal strand-displacement amplification, PCR, qPCR, RT-PCR, degenerate oligonucleotide PCR, or primer extension pre-amplification.

As used herein, a "mixed sample" comprises DNA from at least two sources. In some embodiments, the mixed sample comprises a first population and a second population of nucleic acids. In some embodiments the first population of nucleic acids is mammalian DNA and the second population of nucleic acids in microbial DNA. In some embodiments, the first population of nucleic acids is mammalian mitochondrial DNA and the second population of nucleic acids is bacterial DNA. In some embodiments, the first population of nucleic acids is host DNA and the second population of nucleic acids is non-host DNA. In some embodiments, the first population and the second population of nucleic acids are both microbial DNA. In some embodiments, the first population and second population of nucleic acids are both bacterial DNA.

As used herein, the term "relative incidence" refers to the relative incidence of a nucleotide sequence in a first population of DNA relative to a second population of DNA. The relative incidence can be calculated by dividing (a) the incidence of the nucleotide sequence in the first population, by (b) the incidence of the nucleotide sequence in the second population. The incidence of the nucleotide sequence in each population can be estimated by dividing (a) the amount of DNA (e.g., number of bp) in the population corresponding to the nucleotide sequence (including duplicate copies), by (b) the total amount of DNA (e.g., number of bp) in the population. The relative incidence can be approximated based upon knowledge of whole or partial genome sequences or experimentally. For example, a nucleotide sequence of X bp occurring in Y copies in a genome of G bp would have an incidence of XY/G.

As used herein, "bacteremia" refers to the presence of bacteria in the blood. In some embodiments, the bacteria present in the blood are infectious bacteria that cause disease in a host.

As used herein, "complementary" refers to the ability of a polynucleotide sequence to selectively bind to or anneal to another polynucleotide sequence. The blocking oligonucleotides (e.g., Assassin Blocker or Winged Blocker oligonucleotides) of the present invention are complementary to sequences of one population of DNA in a mixed sample.

As used herein "blocking oligonucleotides" refer to polymers of nucleotide bases which bind and inhibit the amplification of a complementary nucleotide sequence. In some embodiments, blocking oligonucleotides are Assassin Blockers which bind to and inhibit the amplification of a complementary nucleotide sequence due to the formation of interstrand cross-links between the Assassin Blocker and complementary nucleotide sequences. In some embodiments, the blocking oligonucleotides are Winged Blockers which bind to and inhibit the amplification of a complementary nucleotide sequence due to lack of binding at the 5' and 3' ends of the Winged Blockers.

As used herein, "interstrand cross-links" refer to covalent linkages between DNA bases on opposite strands of a DNA double-helix. These cross-links are highly stable and block DNA amplification, requiring excision of the cross-linked nucleotides to continue amplification. In some embodiments of the invention, Assassin Blocker oligonucleotides are cross-linked to mammalian mitochondrial DNA, thereby blocking amplification. In some embodiments, interstrand cross-links are formed between a modified nucleotide base comprising a psoralen chemical group and a complementary nucleotide base in the mammalian mitochondrial DNA.

As used herein, "psoralen" refers to a natural compound which forms DNA interstrand cross-links by intercalating into DNA at 5'-AT sequences, wherein the psoralen binds and forms thymidine adducts with the thymidine nucleotide in the presence of UVA irradiation.

As used herein, the term "spacer" means a chemical moiety that can be covalently bound to the deoxyribose 3' position of the nucleotide at the 3' end of an oligonucleotide such that the 3' position is not available to react with the 5' phosphate of another nucleotide to form a 5'->3' phosphodiester bond between the nucleotides. Therefore, the spacer prevents a DNA polymerase from extending the oligonucleotide by template-dependent DNA synthesis and prevents the oligonucleotide for serving as a primer for DNA synthesis or amplification. Suitable spacers are typically low molecular weight aliphatic moieties that can react with the 3' OH of an oligonucleotide and are commercially available in a variety of forms (e.g., 3' Amino Modifier™, C3 Spacer™, Spacer 9™, Spacer 18™, dSpacer™ from Integrated DNA Technologies, Skokie, Ill.), the simplest of which are of the form —$(CH_2)n$-R where n is 2-10 and R can be —H, —OH, —SH, —NH2. Spacers can also be cyclic aliphatic moieties such as a 3' deoxyribose.

Principles of the Invention.

The present invention depends, in part, upon the development of improved methods to selectively or preferentially amplify a population of nucleic acids (e.g., microbial nucleic acids, including pathogenic microbial DNA), in a mixed clinical sample comprising at least two populations of nucleic acids to aid in the rapid and efficient identification of microbes, including pathogenic microbes, present in the mixed sample. In some embodiments, the method employs blocking oligonucleotides that are cross-linked to certain sequences of the first population of nucleic acids (e.g., mammalian, mitochondrial, or host nucleic acids) to suppress amplification of that first population of nucleic acids and thereby enhance enrichment of the second population of nucleic acids (e.g., microbial, bacterial or non-host nucleic acids). In other embodiments, the method employs blocking oligonucleotides that comprise Winged Helix domains which bind to and suppress the amplification of certain sequences of the first population of nucleic acids (e.g., mammalian, mitochondrial, or host DNA) to suppress amplification of that first population of nucleic acids and thereby enhance enrichment of the second population of nucleic acids.

In one aspect, the invention provides methods of choosing DNA sequences from a first population of DNA (e.g., mammalian DNA) that can advantageously be blocked from amplification to enhance enrichment of the desired second population of nucleic acids (e.g., microbial, bacterial, or non-host nucleic acids). Suitable candidates for Assassin Blocker sequences ("candidate blocking sequences") are selected such that the Assassin Blockers preferentially amplify the second population of nucleic acids (e.g., microbial, bacterial, or non-host DNA) over the first population of nucleic acids (e.g., mammalian, mitochondrial, or host DNA). A candidate blocking sequence should appear more frequently in the first population of nucleic acids (e.g., mammalian, mitochondrial, or host DNA) relative to the second population of nucleic acids (e.g., microbial, bacterial, or non-host DNA). For example, the first 6 nucleotides of the candidate blocking sequence should be between 2 and 50 times more frequent in the first population of nucleic acids compared to the second population of nucleic acids. Furthermore, the first 23 nucleotides of the candidate blocking oligonucleotide sequence should be present in the first population of nucleic acids (e.g., mammalian, mitochondrial, or host DNA) and absent or very rare in the second population of nucleic acids (e.g., microbial, bacterial, or non-host DNA), relative to the first population of nucleic acids. A candidate blocking sequence must also be capable of annealing to the complementary sequence at reasonable temperatures for hybridization (e.g., between 25-50° C.). Candidate blocking sequences may also need to contain certain motifs in order to facilitate cross-linking by the crosslinker (for example A's and T's at a specific end for psoralen). The set of candidate blocker sequences must in aggregate be spaced across the first population of nucleic acids (e.g., mammalian, mitochondrial, or host genome) in such a way that they will block large regions of the population of nucleic acids, if the whole population of nucleic acids is to be suppressed in its amplification. Each population of nucleic acids to be blocked in the mixed sample must be examined individually as the blocking sequences which are suitable for one population of nucleic acids may not extend to another population of nucleic acids. If only a small number of Assassin Blockers are desired for the application, and the first population of nucleic acids is large, the number of regions that a candidate blocking sequence will block in the first population of nucleic acids is also quantified by the algorithm, and sequences which block more regions are preferred.

Thus, the blocking oligonucleotides employed in the invention define a blocked set of the first population of nucleic acids (e.g., mammalian, mitochondrial, or host) DNA sequences which are not amplified, or are amplified to a lesser degree than other populations of nucleic acid sequences in the mixed sample. The result is an amplified sample of DNA which is enriched for the second population of DNA (e.g., microbial, bacterial, or non-host DNA), possible including pathogenic microbial DNA which aids in diagnosis of a pathogenic microbial infection.

In some embodiments, the first population of nucleic acids comprises mammalian mitochondrial DNA sequences. Because mammalian cells include many mitochondria, and because mitochondria typically contain multiple copies of the mitochondrial genome, the copy number of the mitochondrial genome per mammalian cell can be quite high. For example, mtDNA copy number has been estimated to range from hundreds to several thousands of copies per cell (Hosgood et al. (2010), "Mitochondrial DNA copy number and lung cancer risk in a prospective cohort study," *Carcinogenesis,* 31(5):847-849). However, some mitochondrial sequences are substantially similar to pathogenic microbial sequences. Therefore, not all mitochondrial sequences should be included in the first population of blocked sequences because such pathogenic microbial sequences would also be blocked.

Similarly, in some embodiments, the first population of nucleic acids includes mammalian DNA sequences. However, some mammalian sequences are substantially similar to pathogenic microbial sequences. Therefore, not all mammalian sequences should be included in the first population of nucleic acids because such pathogenic microbial sequences would also be blocked.

In some embodiments, at least 5%, 10%, 20%, 30%, 40% or 50% of the blocking oligonucleotides will block mammalian mitochondrial DNA sequences. In some embodiments, less than 5%, 10%, 20%, 30%, 40%, 50%, 60%, 70% or 80% of the blocking oligonucleotides will block mammalian mitochondrial DNA sequences.

In some embodiments, at least 5%, 10%, 20%, 30%, 40% or 50% of the blocking oligonucleotides will block mammalian DNA sequences. In some embodiments, less than 5%, 10%, 20%, 30%, 40%, 50%, 60%, 70% or 80% of the blocking oligonucleotides will block mammalian DNA sequences.

In some embodiments, at least 5%, 10%, 20%, 30%, 40% or 50% of the blocking oligonucleotides will block mammalian mitochondrial DNA sequences and/or mammalian DNA sequences. In some embodiments, less than 5%, 10%, 20%, 30%, 40%, 50%, 60%, 70%, or 80% of the blocking oligonucleotides will block mammalian mitochondrial DNA sequences and/or mammalian DNA sequences.

Pathogenic Microbes.

In some aspects, the present invention provides an improved method for enrichment of a second population of nucleic acids (e.g., microbial, bacterial, or non-host) DNA in an amplified sample of DNA produced by amplification of a mixed sample comprising at least two populations of nucleic acids.

In some embodiments of the present invention, the microbes are bacteria. Although bacteria are normally present in healthy mammals, disruption of the normal balance between the bacteria and the mammalian host, or the presence of abnormal or pathogenic bacteria within the host, can lead to infection.

*Staphylococcus aureus* (*S. aureus*) is a bacterium that is normally present in the human body and is frequently found in the nose, respiratory tract, and on the skin. Although *S. aureus* is not always pathogenic, it is a common cause of skin infections including abscesses, respiratory infections, and food poisoning. The common method of treating *S.*

*aureus* infections is using antibiotics, although the emergence of antibiotic-resistant strains of *S. aureus* such as methicillin-resistant *S. aureus* (MRSA) and vancomycin-resistant *S. aureus* (VRSA) have become worldwide clinical health challenges.

*Staphylococcus epidermidis* (*S. epidermidis*) is a bacterium that is normally present in the human body, where it is frequently found on the skin. Although *S. epidermidis* is not generally pathogenic, subjects with compromised immune systems are at risk of developing *S. epidermidis* infections, and *S. epidermidis* poses a particular threat to subjects with surgical implants because it can grow on plastic surfaces and spread to the human body. *S. epidermidis* strains are often resistant to antibiotics, including rifamycin, fluoroquinolones, gentamicin, tetracycline, clindamycin, and sulfonamides.

*Streptococcus agalactiae* (*S. agalactiae*) is a bacterium that is generally not pathogenic and can be found in the gastrointestinal and genitourinary tract in up to 30% of humans. Pathogenic infections due to *S. agalactiae* are of concern for neonates and immunocompromised individuals. *S. agalactiae* infections in adults can be life-threatening and include bacteremia, soft-tissue infections, osteomyelitis, endocarditis, and meningitis. *S. agalactiae* is increasingly resistant to clindamycin and erythromycin.

*Enterococcus faecalis* (*E. faecalis*) is a bacterium that inhabits the gastrointestinal tracts of humans and other mammals. However, *E. faecalis* can cause endocarditis, septicemia, urinary tract infections, and meningitis. *E. faecalis* infections can be life-threatening, particularly when the *E. faecalis* is resistant to treatment with gentamicin and vancomycin.

*Enterococcus faecium* (*E. faecium*) is a bacterium that inhabits the gastrointestinal tracts of humans and other mammals, but it may also be pathogenic, resulting in diseases such as meningitis and endocarditis. *E. faecium* infections can be life-threatening, particularly when the *E. faecium* is resistant to treatment with vancomycin.

*Escherichia coli* (*E. coli*) is a bacterium that inhabits the gastrointestinal tracts of humans and other mammals, but it may also be pathogenic, resulting in conditions such as gastroenteritis, urinary tract infections, neonatal meningitis, hemorrhagic colitis, and bacteremia. *E. coli* is increasingly resistant to multiple antibiotics, including fluoroquinolones, cephalosporins, and carbapenems.

*Klebsiella pneumoniae* (*K. pneumoniae*) is a bacterium that is normally found in the mouth, skin, and intestines of humans and other mammals. However, it can cause destructive changes to human and mammal lungs if inhaled, particularly to alveoli. *K. pneumoniae* infections are generally seen in subjects with a compromised immune system, including subjects with diabetes, alcoholism, cancer, liver disease, chronic obstructive pulmonary diseases, glucocorticoid therapy, and renal failure. *K. pneumoniae* is increasingly resistant to multiple antibiotics, including fluoroquinolones, cephalosporins, tetracycline, chloramphenicol, carbapenem, and trimethoprim/sulfamethoxazole.

In some embodiments, the microbe is a pathogenic microbe. In some embodiments, the microbe is a bacterium. In some embodiments, the bacterium is associated with bacteremia. In some embodiments, the bacterium is *S. aureus*, *S. epidermidis*, *S. agalactiae*, *E. faecalis*, *E. faecium*, *E. coli*, *K. pneumoniae* or any other bacterial species associated with clinical infection.

Mammalian DNA.

The physical compositions of bacterial and mammalian DNA are distinct although both utilize the same basic genetic code. For example, bacterial DNA is found freely floating in the cytoplasm of the cell rather than within the nucleus or mitochondria, is not bound by histone proteins, contains few repetitive sequences, and is circular rather than linear in shape. These and other differences can be utilized to separate the bacterial DNA from mammalian DNA.

Mammalian cells comprise an additional genome separate from the nuclear DNA known as "mammalian mitochondrial DNA". Mitochondrial DNA is a small, circular, double-stranded DNA molecule in the mitochondria with genes that encode numerous mitochondrial proteins. The mitochondrial DNA is distinct from both mammalian nuclear and bacterial DNA, with more repetitive sequences than bacterial but less than mammalian nuclear DNA. Each mammalian cell contains about 100 mitochondrial DNA molecules compared with only 2-4 complete sets of chromosomes.

In some embodiments, there is at least a 50% reduction in the first population of nucleic acids (e.g., mammalian, mitochondrial, or host) in mixed samples treated with the improved method of the present invention. In some embodiments, there is at least a 60%, at least a 70%, at least an 80%, at least a 90%, at least a 95%, at least a 99%, or at least a 99.99% reduction in the first population of nucleic acids (e.g., mammalian, mitochondrial, or host) in mixed samples treated with the improved method of the present invention. In some embodiments, there is between 90% and 99.99% reduction in mitochondrial DNA in samples treated with the improved method of the present invention. In some embodiments, there is at least 90% reduction in mitochondrial DNA. In some embodiments, there is 90% reduction, 90.5% reduction, 91% reduction, 91.5% reduction, 92% reduction, 92.5% reduction, 93% reduction, 93.5% reduction, 94% reduction, 94.5% reduction, 95% reduction, 95.5% reduction, 96% reduction, 96.5% reduction, 97% reduction, 97.5% reduction, 98% reduction, 98.5% reduction, 99% reduction, or 99.5% reduction in the first population of nucleic acids (e.g., mammalian, mitochondrial, or host) in samples treated with the improved methods of the invention.

Mixed Samples.

In some aspects, the present invention provides an improved method for enrichment a second population of nucleic acids (e.g., microbial, bacterial, or non-host DNA) in a mixed sample of at least two populations of nucleic acids. As used herein, "enrichment" refers to the increase of one population of DNA (e.g., microbial DNA) relative to a second population (e.g., mammalian DNA) in a mixed sample comprising at least two populations of DNA. As used herein, a "mixed sample" comprises DNA from at least two distinct sources. In some embodiments, the mixed sample comprises a first population of nucleic acids (e.g., mammalian, mitochondrial, or host) and a second population of nucleic acids (e.g., microbial, bacterial, or non-host) As used herein, "host DNA" refers to DNA derived from a mammal and "non-host DNA" refers to DNA derived from a microbe. In some embodiments, the mixed sample comprises mammalian and non-mammalian DNA. In some embodiments, the mixed sample comprises mammalian mitochondrial DNA and microbial DNA.

Mixed samples comprising at least one microbial DNA population and at least one mammalian DNA population are obtained from subjects with an infection. The rapid identification of the microbial species present in the mixed sample is critical to treating the infection with the appropriate antimicrobials. This is particularly crucial with bacterial infections because of the number of antibiotic-resistant bacterial strains emerging in recent years. Identification of the microbial species present and treatment with the appropriate antimicrobial can lessen the duration and severity of an infection and possibly prevent death.

In some embodiments, the mixed sample of a first population of nucleic acids (e.g., mammalian, mitochondrial, or host) and a second population of nucleic acids (e.g., microbial, bacterial, or non-host) is obtained or derived from blood, sputum, urine, mucus, saliva, tissue abscess, wound drainage, stool lymph, lavage, cerebral-spinal fluid, or any fluid aspirate or tissue extraction of human and/or other eukaryotic origin. In some embodiments, the mixed sample comprises microbial and mammalian DNA. In some embodiments, the mixed sample of microbial and mammalian DNA is blood.

In some embodiments, the mixed sample comprises DNA from between 10 and $10^8$ microbial genomes per milliliter. In some embodiments, there is DNA from between 10 and $10^3$ microbial genomes per milliliter in the mixed sample. In some embodiments, there is DNA from between $10^3$ and $10^5$ microbial genomes per milliliter in the mixed sample. In some embodiments, there is DNA from between $10^5$ and $10^6$ microbial genomes per milliliter in the mixed sample.

In some embodiments, the mixed sample is obtained or derived from a human subject.

Nucleic Acid Amplification.

The present invention provides methods of amplifying a nucleic acid population. As used herein, "amplification" refers to a process of increasing a population of nucleic acids. Amplification of a nucleic acid population is generally performed prior to identification of the source of nucleic acids (e.g., mammalian DNA, microbe DNA). Non-limiting examples of nucleic acid amplification techniques known in the art include: polymerase chain reaction (PCR), quantitative PCR (qPCR), reverse-transcriptase PCR (RT-PCR), degenerate oligonucleotide PCR, primer extension pre-amplification, strand displacement amplification (SDA), or transcription mediated amplification (TMA).

Amplification of one population of nucleic acids by any of the previously-mentioned methods requires a primer and a polymerase. As used herein, a "primer" is an oligonucleotide that is complementary to a sequence in the population of nucleic acids to be amplified. As used herein, "complementary" refers to the ability of a nucleotide sequence to base-pair with another nucleotide sequence. Base-pairing may be by Watson-Crick base pairing, Hoogsteen base pairing, or any other method of base-pairing known in the art. As used herein, a "polymerase" is an enzyme that synthesizes long stretches of nucleic acids, including DNA and RNA, by extending a primer. Polymerases utilize an existing nucleic acid strand as a template for nucleic acid synthesis and typically employ Watson-Crick base pairing to select the correct nucleotide to add to the growing nucleic acid strands, wherein adenine (A) pairs with thymine (T), A pairs with uracil (U), and cytosine (C) pairs with guanosine (G). Non-limiting examples of polymerases include eukaryotic polymerases such as polymerase alpha, polymerase delta, and polymerase epsilon; bacterial polymerases include *Thermus aquaticus* (Taq), Deep Vent, and Therminator; RNA polymerases such as RNA polymerase I and RNA polymerase II; and strand-displacing polymerases.

As used herein, a "strand-displacing polymerase" refers to an enzyme which separate the strands of a DNA double helix as it extends a primer template. In some embodiments, the strand displacement polymerase is selected from the group consisting of: phi29 polymerase; Bst DNA polymerase, large Fragment™; Bsu DNA polymerase, large Fragment™; Deep Vent DNA Polymerase®; Deep Vent (exo) DNA Polymerase®; Klenow fragment; DNA polymerase I, large fragment; M-MuLV reverse transcriptase; Therminator DNA Polymerase®; Vent DNA Polymerase®; Vent (exo) DNA Polymerase®; and SD polymerase. As used herein, "phi29" refers to the replicative polymerase from the *Bacillus subtilis* phage phi29. The phi29 polymerase has exceptional strand displacement and processive synthesis properties, as well as an inherent 3'→5' exonuclease proofreading ability.

In some aspects, the present invention provides methods for the selective amplification of one population of nucleic acids in a mixed sample. "Selective amplification" refers to the amplification of one population of nucleic acids relative to another population of nucleic acids. Non-limiting methods of selective nucleic acid amplification in a mixed sample include digestion of a DNA sample with a nuclease and inhibition of amplification of one population of nucleic acids.

In some embodiments, selective amplification of one population of nucleic acids in a mixed sample takes advantage of sequences found more frequently in a first population of nucleic acids (e.g., mammalian, mitochondrial, or host DNA) relative to a second population of nucleic acids (e.g., microbial, bacterial, or non-host DNA). In some embodiments, the first population of nucleic acids comprises mammalian DNA sequences. These mammalian DNA sequences may be nuclear and/or mitochondrial DNA sequences. In some embodiments, the mammalian DNA sequence is found in mammalian mitochondrial DNA. In some embodiments, the mammalian DNA sequence is found in mammalian nuclear DNA.

In some aspects, the present invention provides an improved method of amplifying a second population of nucleic acids (e.g., microbial, bacterial, or non-host) in a mixed sample comprising at least two populations of nucleic acids. In some embodiments, the first population of nucleic acids is mammalian DNA and the second population of nucleic acids is microbial DNA. In some embodiments, the amplification of microbial DNA is increased by between 10-fold and 100-fold compared with samples not treated with the improved method of the present invention. In some embodiments, the amplification of microbial DNA is increased by 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold compared with samples not treated with the improved method of the present invention. In some embodiments, the amplification of microbial DNA is increased by at least 10-fold compared with samples not treated with the improved method of the present invention. In some embodiments, the amplification of microbial DNA is increased by less than 100-fold compared with samples not treated with the improved method of the present invention.

In some embodiments, the amplification is performed using a strand-displacing polymerase selected from the group comprising: phi29 polymerase; Bst polymerase, large Fragment™; Bsu DNA polymerase, large Fragment™; Deep Vent DNA Polymerase®; Deep Vent (Exo) DNA Polymerase®; Klenow fragment; DNA polymerase I, large fragment; M-MuLV reverse transcriptase; Therminator DNA Polymerase®; Vent DNA Polymerase®; Vent (exo) DNA Polymerase®, and SD polymerase. In some embodiments, the amplification is by phi29 polymerase.

In some embodiments, nucleic acid amplification is whole genome amplification (WGA). Different and novel approaches to WGA have been developed since its inception in 1992, including degenerate oligonucleotide primed-polymerase chain reaction (DOP-PCR), multiple displacement amplification (MDA), and multiple annealing and looping-based amplification cycles (MALBAC) [3]. MDA by phi29 DNA polymerase has become the preferred method because it utilizes isothermal amplification in which phi29 strand displaces the double stranded DNA it encounters during DNA synthesis.

A key aspect of WGA by phi29 is usage of random hexamer oligonucleotides to amplify all possible genomic sequences. While this is crucial for an unbiased DNA amplification approach, the use of random hexamers becomes a liability when dealing with samples of pathogenic microbial DNA isolated from a human biological sample due to undesired human nucleic acid contaminants. The human genome is approximately 1,000 times larger than the average microbial genome, which presents a daunting challenge when sequencing pathogenic microbes that are vastly outnumbered by human cells. Although physical and chemical approaches are partially effective in depleting human chromosomal DNA, human mitochondrial DNA (mtDNA) contamination has proven to be more difficult to remove [4]. Mitochondrial DNA contamination could represent as much as 30% of all reads sequenced because of the circular nature and the high copy number of mtDNA per cell. The prevention of mtDNA amplification from biological samples during MDA improves the efficiency of pathogenic microbial sequencing, which is critical clinically.

Blocking Oligonucleotides.

In some embodiments, the present invention provides oligonucleotides comprising 6-50 nucleotides comprising a sequence that occurs more frequently in a first population of nucleic acids compared to a second population of nucleic acids. In some embodiments, the relative incidence of the sequence in the first population of nucleic acids relative to the second population of nucleic acids is at least 50. As used herein, the "relative incidence" refers to the frequency with which a sequence occurs in one population of nucleic acids relative to another.

In some embodiments, the oligonucleotides are blocking oligonucleotides. As used herein, "blocking oligonucleotides" refer to polymers of nucleotide bases which specifically bind to and inhibit the amplification of a complementary nucleotide sequence. In some embodiments, blocking oligonucleotides are Assassin Blocker oligonucleotides which bind and inhibit the amplification of a complementary nucleotide sequence due to the formation of interstrand cross-links between the Assassin Blocker and complementary nucleotide sequences.

In some embodiments, the Assassin Blocker oligonucleotide sequence is complementary to a first population of nucleic acids. In some embodiments, the first population of nucleic acids is derived from mammalian DNA sequences. In some embodiments, the Assassin Blocker oligonucleotide is complementary to a mammalian nuclear DNA sequence. In some embodiments, the Assassin Blocker oligonucleotide is complementary to a mammalian mitochondrial DNA sequence.

As used herein, "interstrand cross-links" refer to covalent linkages between DNA bases on opposite strands of a DNA double-helix. These cross-links are stable and block separation of the DNA strands, thereby blocking amplification until the cross-linked nucleotides are excised. Non-limiting examples of cross-linking agents include: psoralen, cisplatin, mitomycin C, aldehydes, nitrous acids, and reactive oxygen species. In some embodiments of the present invention, Assassin Blocker oligonucleotides are cross-linked to a targeted population of DNA, thereby blocking amplification. In some embodiments, interstrand cross-links are formed between a modified nucleotide base comprising a psoralen chemical group and a complementary nucleotide base in the targeted population of DNA.

As used herein, "psoralen" refers to a natural compound which forms DNA interstrand cross-links by intercalating into DNA at 5'-AT sequences, whereby the psoralen binds and forms thymidine adducts with the thymidine nucleotide in the presence of UVA irradiation. As a DNA interstrand cross-linker, psoralen plus UVA (PUVA) therapy is utilized to treat hyperproliferative skin disorders including psoriasis and certain types of skin cancers.

In some embodiments, the blocking oligonucleotides are Winged Blockers which bind and inhibit the amplification of a complementary nucleotide sequence. As used herein "Winged Blockers" are oligonucleotides which bind to and block the amplification of complementary DNA due to lack of binding at the 5' and 3' ends of the Winged Blockers. This lack of binding on the 5' and 3' ends prohibits a polymerase from binding and separating the two nucleic acid strands, thereby blocking amplification.

In some embodiments, the blocking oligonucleotide comprises a spacer. The spacer prevents a polymerase binding and thus blocks amplification of the complementary nucleic acid strand. In some embodiments, the blocking oligonucleotide comprises a C2, C3, C4, C5, C6, C7, C8, C9, C10, C11, or C12 spacer. The spacer of the Assassin Blocker oligonucleotide prevents DNA synthesis from the 3' end of the blocking oligonucleotide.

In some aspects, the present invention provides a blocking oligonucleotide comprising (a) at least 15 contiguous nucleotides that are complementary to a sequence that is observed more frequently within a first population of nucleic acids (e.g., mammalian, mitochondrial, or host) per kilobase compared to a second population of nucleic acids (e.g., microbial, bacterial or non-host) and (b) at least one modified nucleotide that cross-links to a complementary sequence.

In some embodiments, the mammalian genome is a mitochondrial genome. In some embodiments, the bacterial genome is *Staphylococcus aureus, Staphylococcus epidermidis, Streptococcus agalactiae, Enterococcus faecalis, Enterococcus faecium, Escherichia coli*, and *Klebsiella pneumoniae*. In some embodiments, a modified nucleotide is a 5' modified nucleotide. In some embodiments, the modified nucleotide is a psoralen nucleotide. In some embodiments a modified nucleotide is a 5' modified nucleotide.

In some embodiments, the blocking oligonucleotide comprises at least 15 contiguous nucleotides that are complementary to a sequence that is observed more frequently within a first population of nucleic acids (e.g., mammalian, mitochondrial, or host) per kilobase compared to a second population of nucleic acids (e.g., microbial, bacterial, or non-host). In some embodiments, the blocking oligonucleotide comprises at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 contiguous nucleotides that are complementary to a sequence that is observed more frequently within a first population of nucleic acids (e.g., mammalian, mitochondrial, or host) per kilobase compared to a second population of nucleic acids (e.g., microbial, bacterial, or non-host). In some embodiments, the first population of nucleic acids is mammalian DNA and the second population of nucleic acids is microbial DNA.

In some embodiments, the blocking oligonucleotide comprises at least 15 nucleotides. In some embodiments, the blocking oligonucleotide comprises at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, at least 30 nucleotides, at least 31 nucleotides, at least 32 nucleotides, at least 33 nucleotides, at least 34 nucleotides, at least 35 nucleotides, at least 36 nucleotides, at least 37 nucleotides, at least 38 nucleotides, at least 39 nucleotides, at least 40 nucleotides, at least 41 nucleotides, at least 42 nucleotides, at least 43 nucleotides, at least 44 nucleotides, at least 45 nucleotides, at least 46 nucleotides, at least 47 nucleotides, at least 48 nucleotides, at least 49 nucleotides, or at least 50 nucleotides. In some embodiments, the blocking oligonucleotide comprises between 15 and 50 nucleotides. In some embodiments, the blocking oligonucleotide comprises 50 nucleotides. In some embodiments, the blocking oligonucleotide comprises between and 50 nucleotides. In some embodiments, the blocking oligonucleotide comprises between 15 and 35 nucleotides. In some embodiments, the blocking oligonucleotide comprises between 15 and nucleotides.

In some embodiments, the blocking oligonucleotide is at least 50% complementary to a sequence that is observed more frequently in the first population of nucleic acids (e.g., mammalian, mitochondrial, or host nucleic acids). In some embodiments, the blocking oligonucleotide is at least 55% complementary to a sequence that is observed more frequently in the first population of nucleic acids (e.g., mammalian, mitochondrial, or host nucleic acids). In some embodiments, the blocking oligonucleotide is at least 60% complementary to a sequence that is observed more frequently in the first population of nucleic acids (e.g., mammalian, mitochondrial, or host nucleic acids). In some embodiments, the blocking oligonucleotide is at least 65% complementary to a sequence that is observed more frequently in the first population of nucleic acids (e.g., mammalian, mitochondrial, or host nucleic acids). In some embodiments, the blocking oligonucleotide is at least 70% complementary to a sequence that is observed more frequently in the first population of nucleic acids (e.g., mammalian, mitochondrial, or host nucleic acids). In some embodiments, the blocking oligonucleotide is at least 75% complementary to a sequence that is observed more frequently in the first population of nucleic acids (e.g., mammalian, mitochondrial, or host nucleic acids). In some embodiments, the blocking oligonucleotide is at least 80% complementary to a sequence that is observed more frequently in the first population of nucleic acids (e.g., mammalian, mitochondrial, or host nucleic acids). In some embodiments, the blocking oligonucleotide is at least 85% complementary to a sequence that is observed more frequently in the first population of nucleic acids (e.g., mammalian, mitochondrial, or host nucleic acids). In some embodiments, the blocking oligonucleotide is at least 90% complementary to a sequence that is observed more frequently in the first population of nucleic acids (e.g., mammalian, mitochondrial, or host nucleic acids). In some embodiments, the blocking oligonucleotide is at least 95% complementary to a sequence that is observed more frequently in the first population of nucleic acids (e.g., mammalian, mitochondrial, or host nucleic acids). In some embodiments, the blocking oligonucleotide is at least 99% complementary to a sequence that is observed more frequently in the first population of nucleic acids (e.g., mammalian, mitochondrial, or host nucleic acids).

In some embodiments, the blocking oligonucleotide comprises a sequence as set forth in SEQ ID NOs: 1-16. In some embodiments, the blocking oligonucleotide is complementary to a sequence as set forth in SEQ ID NOs: 17-32.

In some embodiments the blocking oligonucleotide comprises a Winged Blocker at the 5' end. In some embodiments the blocking oligonucleotide comprises a Winged Blocker at the 3' end. In some embodiments, the blocking oligonucleotide comprises a Winged Blocker at 5' end and the 3' end. In some embodiments, the Winged Blocker comprises between 5 and 15 nucleotides that are not complementary to the first population of nucleic acids (e.g., mammalian, mitochondrial, or host genome). In some embodiments, the Winged Blocker comprises 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, or 15 nucleotides. In some embodiments, the Winged Blocker comprises between 8 and 15 nucleotides. In some embodiments, the Winged Blocker comprises between 5 and 10 nucleotides.

In some embodiments, the modified oligonucleotide further comprises an interstrand cross-linking agent that cross-links the oligonucleotide to the first population of nucleic acids (e.g., mammalian, mitochondrial, or host). In some embodiments, the cross-linking agent is photoactivated. In some embodiments, the cross-linking agent is psoralen. In some embodiments, the first population of nucleic acids is mammalian DNA. In some embodiments, the mammalian DNA is mitochondrial DNA.

In some embodiments, the present invention provides an improved method for enrichment of a second population of nucleic acids (e.g., microbial, bacterial, or non-host DNA) in an amplified sample of DNA produced by amplification of a mixed sample of a first population of nucleic acids (e.g., mammalian, mitochondrial, or host) and a second population of nucleic acids (e.g., microbial, bacterial, or non-host). In some embodiments, the first population of nucleic acids is mammalian DNA and the second population of nucleic acids is microbial DNA. In some embodiments, the amplification of mammalian DNA is suppressed by adding to the mixed sample at least one blocking oligonucleotide which specifically binds to at least one mammalian DNA in the mixed sample and suppresses amplification of the mammalian DNA. In some embodiments, the improved method comprises adding a set of at least two blocking oligonucleotides to the mixed sample that are roughly equally distributed across the mammalian genome. In some embodiments, the set of blocking oligonucleotides comprises between 2 and $10^8$ blocking oligonucleotides. In some embodiments, the mammalian DNA is mammalian mitochondrial DNA.

In some aspects, the present invention provides a composition comprising at least one blocking oligonucleotide comprising a) at least 15 contiguous nucleotides that are complementary to a sequence that is observed more frequently within a first population of nucleic acids (e.g., mammalian, mitochondrial, or host) per kilobase compared to a second population of nucleic acids (e.g., microbial, bacterial, or non-host) and (b) at least one modified nucleotide that cross-links to a complementary sequence and an interstrand cross-linking agent. In some embodiments, the composition comprises between 2 and $10^8$ blocking oligonucleotides.

In some aspects, the present invention provides a kit comprising the composition and a strand-displacing polymerase. In some embodiments, the strand-displacing polymerase is phi29 polymerase.

Medical Conditions and Treatment.

Methods and oligonucleotides of the present invention can be used in the diagnosis and treatment of medical conditions including infection by pathogenic microbes. In some embodiments, methods and oligonucleotides of the present invention are used to identify a pathogenic microbe(s) causing an infection in a subject. The pathogenic microbe(s) can be a bacterium, a virus, a fungus, a protist, or a yeast. Methods of the present invention provide suppression of amplification of mammalian DNA in a mixed sample. In some embodiments, the mixed sample is a clinical sample from the subject, optionally wherein the clinical sample is blood, sputum, blood, sputum, urine, mucus, saliva, tissue abscess, wound drainage, stool, lymph, lavage, cerebral-spinal fluid, or any fluid aspirate or tissue extraction of human and/or other eukaryotic origin.

In some embodiments, methods and oligonucleotides of the present invention are used to identify a pathogenic microbe selected from: *Achromobacter* spp., *Acinetobacter calcoaceticus/baumannii* complex, *Acinetobacter haemolyticus*, *Acinetobacter junii*, *Acinetobacter radioresistens*, *Acinetobacter ursingii*, *Acinetobacter lwoffii*, *Actinomyces israelii*, *Actinomyces meyeri*, *Actinomyces naeslundii*, *Actinomyces neuii*, *Actinomyces odontolyticus*, *Actinomyces pyogenes*, *Actinomyces viscosus*, *Aerococcus urinae*, *Aerococcus viridans*, *Aeromonas* spp., *Alcaligenes faecalis*, *Alcaligenes xylosoxidans*, Alpha hemolytic *streptococcus*, *Arcanobacterium haemolyticum*, *Aspergillus* spp., *Bacillus* spp., *Bacteroides fragilis*, *Bartonella Quintana*, *Blastocystis hominis*, *Bordetella* spp., *Borrelia* spp., *Brevundimonas diminuta*, *Brevundimonas vesicularis* *Brucella* spp., *Burkholderia* spp., *Burkholderia cepacia*, *Burkholderia cepacia* complex, *Burkholderia gladioli*, *Burkholderia multivorans*, *Burkholderia pseudomallei*, *Burkholderia vietnamiensis*, *Campylobacter* spp., *Cedecea davisae*, *Chlamydia pneumoniae*, *Chlamydia psittaci*, *Chlamydia trachomatis*, *Chryseobacterium indologenes*, *Citrobacter* spp., *Citrobacter amalonaticus*, *Citrobacter farmer*, *Citrobacter freundii* complex, *Citrobacter koseri*, *Citrobacter sedlakii*, *Clostridium botulinum*, *Clostridium difficile*, *Clostridium perfringens*, *Clostridium tetani*, Coagulase negative *staphylococcus*, *Corynebacterium diphtheriae*, *Corynebacterium pseudotuberculosis*, *Corynebacterium ulcerans*, *Coxiella* spp., *Cronobacter sakazakii*, *Delftia acidovorans*, *Dermabacter hominis*, *Edwardsiella tarda*, *Ehrlichia* spp., *Eikenella corrodens*, *Enterobacter* spp., *Enterobacter aerogenes*, *Enterobacter cancerogenus*, *Enterobacter cloacae* complex, *Enterobius vermicularis*, *Enterococcus* spp., *Enterococcus avium*, *Enterococcus casseliflavus*, *Enterococcus durans*, *Enterococcus faecalis*, *Enterococcus faecium*, *Enterococcus gallinarum*, *Enterococcus hirae*, *Enterococcus raffinosus*, *Escherichia coli*, *Francisella* spp., *Fusarium* spp., *Gemella* spp., *Granulicatella adiacens*, Group A *streptococcus*, Group B *salmonella*, Group B *streptococcus*, Group C1 *salmonella*, Group C2 *salmonella*, Group C *streptococcus*, Group D *salmonella*, Group G *salmonella*, Group G *streptococcus*, *Haemophilus influenza*, *Haemophilus parainfluenzae*, *Hafnia alvei*, *Helicobacter* spp., *Kingella kingae*, *Klebsiella* spp., *Klebsiella granulomatis*, *Klebsiella oxytoca*, *Klebsiella pneumoniae*, *Kluyvera* spp., *Kocuria kristinae*, *Lactobacillus* spp., *Leclercia adecarboxylata*, *Legionella pneumophila*, *Leishmania* spp., *Leptospira* spp., *Leuconostoc pseudomesenteroides*, *Listeria monocytogenes*, *Micrococcus luteus*, *Moraxella catarrhalis*, *Morganella morganii*, *Mycobacterium abscessus*, *Mycobacterium chimaera*, *Mycobacterium fortuitum*, *Mycobacterium leprae*, *Mycobacterium tuberculosis*, *Mycoplasma genitalium*, *Mycoplasma pneumoniae*, *Neisseria meningitidis*, *Neisseria gonorrhoeae*, *Nocardia* spp., *Ochrobactrum anthropic*, *Orientia tsutsugamushi*, *Pandoraea* spp., *Pantoea* spp., *Pantoea agglomerans*, *Paracoccus yeei*, *Pasteurella canis*, *Pasteurella multocida*, *Pediococcus*, *Peptostreptococcus*, *Plesiomonas shigelloides*, *Prevotella* spp., *Propionibacterium* spp., *Propionibacterium acnes*, *Proteus* spp., *Proteus mirabilis*, *Proteus penneri*, *Proteus vulgaris*, *Providencia rettgeri*, *Providencia stuartii*, *Pseudomonas* spp., *Pseudomonas aeruginosa*, *Pseudomonas fluorescens*, *Pseudomonas putida*, *Pseudomonas stutzeri*, *Rahnella aquatilis*, *Ralstonia* spp., *Raoultella* spp., *Raoultella ornithinolytica*, *Raoultella planticola*, *Rickettsia prowazekii*, *Rickettsia typhi*, *Roseomonas gilardii*, *Rothia mucilaginosa*, *Salmonella* spp., *Scedosporium* spp., *Serratia* spp., *Serratia fonticola*, *Serratia liquefaciens*, *Serratia marcescens*, *Shigella flexneri*, *Shigella sonnei*, *Sphingobacterium* spp., *Staphylococcus aureus*, *Staphylococcus auricularis*, *Staphylococcus capitis*, *Staphylococcus caprae*, *Staphylococcus cohnii*, *Staphylococcus epidermidis*, *Staphylococcus haemolyticus*, *Staphylococcus hominis*, *Staphylococcus intermedius*, *Staphylococcus lugdunensis*, *Staphylococcus pasteuri*, *Staphylococcus saccharolyticus*, *Staphylococcus saprophyticus*, *Staphylococcus schleiferi*, *Staphylococcus simulans*, *Staphylococcus warneri*, *Stenotrophomonas maltophilia*, *Streptococcus* spp., *Streptococcus agalactiae*, *Streptococcus anginosus*, *Streptococcus canis*, *Streptococcus constellatus*, *Streptococcus dysgalactiae*, *Streptococcus intermedius*, *Streptococcus parasanguinis*, *Streptococcus pneumoniae*, *Streptococcus pseudopneumoniae*, *Streptococcus pyogenes*, *Streptococcus salivarius*, *Streptococcus sanguinis*, *Streptococcus vestibularis*, *Treponema* spp., *Trichophyton* spp., *Trichosporon asahii*, *Trueperella bernardiae*, *Tsukamurella tyrosinosolvens*, *Ureaplasma* spp., *Vibrio cholerae*, *Vibrio parahaemolyticus*, *Weissella confuse*, *Yersinia enterocolitica*, *Yersinia pestis*, *Yersinia pseudotuberculosis*, *Yokenella regensburgei*, *Aspergillus fumigatus*, *Candida albicans*, *Candida auris*, *Candida dubliniensis*, *Candida glabrata*, *Candida krusei*, *Candida lusitaniae*, *Candida parapsilosis*, *Candida tropicalis*, *Cryptococcus neoformans*, *Pneumocystis*, *Penicillium*, *Fusarium*, *Microsporum* spp., Mucormycosis, *Histoplasma*, *Blastomyces*, *Coccidioides*, *Trichophyton*, *Trichosporon* spp., *Microsporum*, *Pneumocystis jiroveci*, *Epidermophyton*, *Curvularia*, *Saccharomyces*, *Sporothrix*, *Microsporidia*, Adenoviruses, Alphavirus, Arbovirus, Astrovirus, Bocaviruses, Bunyaviridae, Chikungunya virus, Coronavirus, Coxsackievirus, Cytomegalovirus, Dengue, Echovirus, Ebola, Enterovirus, Epstein-Barr virus, Flaviviridae, Foot-and-mouth disease virus, Hantavirus, Hepatitis A, Hepatitis B, Hepatitis C, Hepatitis E, Herpes simplex virus, Human cytomegalovirus, Human herpesvirus 6, Human herpesvirus 7, Human herpesvirus 8, Human immunodeficiency virus, Human papillomaviruses, Human polyomaviruses, Human T-cell lymphotrophic virus, Influenza, Lassa virus, Marburg virus, Measles virus, Metapneumovirus, Molluscipoxvirus, Morbillivirus, Mumps, Nipah virus, Norovirus, Parainfluenza, Parechovirus, Parvovirus B19, Poliovirus, Polyomavirus, Poxviruses, Rabies virus, Respiratory syncytial virus, Rhinovirus, Rotavirus, Rubella virus, Rubivirus, Sapovirus, Togaviridae, Tick-borne Encephalitis virus, Usutu virus, Vaccinia virus, Varicella zoster virus, Variola virus, West Nile virus, yellow fever virus, and Zika virus.

In some embodiments, the methods and oligonucleotides of the present invention are used to select an appropriate treatment of a pathogenic microbe infection. In some embodiments, a clinical sample is obtained from a subject having or suspected of having a pathogenic microbial infection. In some embodiments, the infection is a bacteremia. In some embodiments, the appropriate treatment is treatment with an antibiotic. Non-limiting examples of antibiotics include: vancomycin, bacterium, methicillin, ceftobiprole, ceftaroline, dalbacancin, daptomycin, fusidic acid, linezolid, mupirocin, oritavancin, tedzolid, telavancin, tetracycline, amoxicillin, penicillin, doxycycline, cephalexin, ciprofloxacin, clindamycin, metronidazole, azithromycin, sulfamethoxazole/trimethoprim, and levofloxacin. In some embodiments, the infection is a viral infection. In some embodiments, the appropriate treatment is an anti-viral. Non-limiting examples of anti-virals include: abacavir, acyclovir, balavir, cidofovir, darunavir, entecavir, famciclovir, ganciclovir, ostellamivir, penciclovir, and zalcitabine. In some embodiments, the infection is a fungal infection. In some embodiments, the appropriate treatment is an anti-fungal. Non-limiting examples of anti-fungals include: amphotericin B, candicidin, filipin, hamycin, natamycin, nystatin, rimocidin, bifonazole, butoconazole, clotrimazole, econazole, fenticonazole, isoconzaole, and anidulafungin.

EXAMPLES

The following examples demonstrate certain embodiments of the present invention. However, it is to be understood that these examples are for illustrative purposes only and do not intend, nor should any be construed, to be wholly definitive as to conditions and scope of this invention. The examples were carried out using standard techniques, which are well-known and routine to those of skill in the art, except where otherwise described in detail.

Example 1

Design of Assassin Blocker DNA Oligonucleotide Sequences

To suppress amplification of a first population of DNA molecules comprising mammalian DNA sequences, Assassin Blocker oligonucleotides were designed to be complementary to DNA sequences that occurred more frequently in the mammalian DNA population than in the microbial DNA population. The mammalian sequences chosen were unique to the first population, with minimal overlap to a second population of DNA to be amplified.

The human mitochondrial genome is small (~16.6 kb), comprising sequences distributed on a plus strand and a minus strand which are unique from both the human nuclear genome and bacterial genomes. Sequences of Assassin Blocker oligonucleotides were designed to be complementary to sequences which had a higher frequency per kilobase (kb) in the mitochondrial genome compared to bacterial, fungal, and viral genomes. Non-limiting examples of bacterial, fungi, and viral genomes include: *Achromobacter* spp., *Acinetobacter calcoaceticus/baumannii* complex, *Acinetobacter haemolyticus, Acinetobacter junii, Acinetobacter radioresistens, Acinetobacter ursingii, Acinetobacter lwoffii, Actinomyces israelii, Actinomyces meyeri, Actinomyces naeslundii, Actinomyces neuii, Actinomyces odontolyticus, Actinomyces pyogenes, Actinomyces viscosus, Aerococcus urinae, Aerococcus viridans, Aeromonas* spp., *Alcaligenes faecalis, Alcaligenes xylosoxidans*, Alpha hemolytic *streptococcus, Arcanobacterium haemolyticum, Aspergillus* spp., *Bacillus* spp., *Bacteroides fragilis, Bartonella Quintana, Blastocystis hominis, Bordetella* spp., *Borrelia* spp., *Brevundimonas diminuta, Brevundimonas vesicularis Brucella* spp., *Burkholderia* spp., *Burkholderia cepacia, Burkholderia cepacia* complex, *Burkholderia gladioli, Burkholderia multivorans, Burkholderia pseudomallei, Burkholderia vietnamiensis, Campylobacter* spp., *Cedecea davisae, Chlamydia pneumoniae, Chlamydia psittaci, Chlamydia trachomatis, Chryseobacterium indologenes, Citrobacter* spp., *Citrobacter amalonaticus, Citrobacter farmer, Citrobacter freundii* complex, *Citrobacter koseri, Citrobacter sedlakii, Clostridium botulinum, Clostridium difficile, Clostridium perfringens, Clostridium tetani*, Coagulase negative *staphylococcus, Corynebacterium diphtheriae, Corynebacterium pseudotuberculosis, Corynebacterium ulcerans, Coxiella* spp., *Cronobacter sakazakii, Delftia acidovorans, Dermabacter hominis, Edwardsiella tarda, Ehrlichia* spp., *Eikenella corrodens, Enterobacter* spp., *Enterobacter aerogenes, Enterobacter cancerogenus, Enterobacter cloacae* complex, *Enterobius vermicularis, Enterococcus* spp., *Enterococcus avium, Enterococcus casseliflavus, Enterococcus durans, Enterococcus faecalis, Enterococcus faecium, Enterococcus gallinarum, Enterococcus hirae, Enterococcus raffinosus, Escherichia coli, Francisella* spp., *Fusarium* spp., *Gemella* spp., *Granulicatella adiacens*, Group A *streptococcus*, Group B *salmonella*, Group B *streptococcus*, Group C1 *salmonella*, Group C2 *salmonella*, Group C *streptococcus*, Group D *salmonella*, Group G *salmonella*, Group G *streptococcus, Haemophilus influenza, Haemophilus parainfluenzae, Hafnia alvei, Helicobacter* spp., *Kingella kingae, Klebsiella* spp., *Klebsiella granulomatis, Klebsiella oxytoca, Klebsiella pneumoniae, Kluyvera* spp., *Kocuria kristinae, Lactobacillus* spp., *Leclercia adecarboxylata, Legionella pneumophila, Leishmania* spp., *Leptospira* spp., *Leuconostoc pseudomesenteroides, Listeria monocytogenes, Micrococcus luteus, Moraxella catarrhalis, Morganella morganii, Mycobacterium abscessus, Mycobacterium chimaera, Mycobacterium fortuitum, Mycobacterium leprae, Mycobacterium tuberculosis, Mycoplasma genitalium, Mycoplasma pneumoniae, Neisseria meningitidis, Neisseria gonorrhoeae, Nocardia* spp., *Ochrobactrum anthropic, Orientia tsutsugamushi, Pandoraea* spp., *Pantoea* spp., *Pantoea agglomerans, Paracoccus yeei, Pasteurella canis, Pasteurella multocida, Pediococcus, Peptostreptococcus, Plesiomonas shigelloides, Prevotella* spp., *Propionibacterium* spp., *Propionibacterium acnes, Proteus* spp., *Proteus mirabilis, Proteus penneri, Proteus vulgaris, Providencia rettgeri, Providencia stuartii, Pseudomonas* spp., *Pseudomonas aeruginosa, Pseudomonas fluorescens, Pseudomonas putida, Pseudomonas stutzeri, Rahnella aquatilis, Ralstonia* spp., *Raoultella* spp., *Raoultella ornithinolytica, Raoultella planticola, Rickettsia prowazekii, Rickettsia typhi, Roseomonas gilardii, Rothia mucilaginosa, Salmonella* spp., *Scedosporium* spp., *Serratia* spp., *Serratia fonticola, Serratia liquefaciens, Serratia marcescens, Shigella flexneri, Shigella sonnei, Sphingobacterium* spp., *Staphylococcus aureus, Staphylococcus auricularis, Staphylococcus capitis, Staphylococcus caprae, Staphylococcus cohnii, Staphylococcus epidermidis, Staphylococcus haemolyticus, Staphylococcus hominis, Staphylococcus intermedius, Staphylococcus lugdunensis, Staphylococcus pasteuri, Staphylococcus saccharolyticus, Staphylococcus saprophyticus, Staphylococcus schleiferi, Staphylococcus simulans, Staphylococcus warneri, Stenotrophomonas maltophilia, Streptococcus* spp., *Streptococcus agalactiae, Streptococcus anginosus, Streptococcus canis, Streptococcus constellatus, Streptococcus dysgalactiae, Streptococcus intermedius, Streptococcus parasanguinis, Streptococcus pneumoniae, Streptococcus pseudopneumoniae, Streptococcus pyogenes, Streptococcus salivarius, Streptococcus san-* guinis, Streptococcus vestibularis, Treponema spp., Trichophyton spp., Trichosporon asahii, Trueperella bernardiae, Tsukamurella tyrosinosolvens, Ureaplasma spp., Vibrio cholerae, Vibrio parahaemolyticus, Weissella confuse, Yersinia enterocolitica, Yersinia pestis, Yersinia pseudotuberculosis, Yokenella regensburgei, Aspergillus fumigatus, Candida albicans, Candida auris, Candida dubliniensis, Candida glabrata, Candida krusei, Candida lusitaniae, Candida parapsilosis, Candida tropicalis, Cryptococcus neoformans, Pneumocystis, Penicillium, Fusarium, Microsporum spp., Mucormycosis, Histoplasma, Blastomyces, Coccidioides, Trichophyton, Trichosporon spp., Microsporum, Pneumocystis jiroveci, Epidermophyton, Curvularia, Saccharomyces, Sporothrix, Microsporidia, Adenoviruses, Alphavirus, Arbovirus, Astrovirus, Bocaviruses, Bunyaviridae, Chikungunya virus, Coronavirus, Coxsackievirus, Cytomegalovirus, Dengue, Echovirus, Ebola, Enterovirus, Epstein-Barr virus, Flaviviridae, Foot-and-mouth disease virus, Hantavirus, Hepatitis A, Hepatitis B, Hepatitis C, Hepatitis E, Herpes simplex virus, Human cytomegalovirus, Human herpesvirus 6, Human herpesvirus 7, Human herpesvirus 8, Human immunodeficiency virus, Human papillomaviruses, Human polyomaviruses, Human T-cell lymphotrophic virus, Influenza, Lassa virus, Marburg virus, Measles virus, Metapneumovirus, Molluscipoxvirus, Morbillivirus, Mumps, Nipah virus, Norovirus, Parainfluenza, Parechovirus, Parvovirus B19, Poliovirus, Polyomavirus, Poxviruses, Rabies virus, Respiratory syncytial virus, Rhinovirus, Rotavirus, Rubella virus, Rubivirus, Sapovirus, Togaviridae, Tick-borne Encephalitis virus, Usutu virus, Vaccinia virus, Varicella zoster virus, Variola virus, West Nile virus, yellow fever virus, and Zika virus. Sequences were chosen every 1 to 2 kilobases from both the plus and minus strands of the mitochondrial genome. Multiple Assassin Blocker oligonucleotides may also be utilized to be complementary to sequences which are roughly equally distributed across the mitochondrial genome to maximize the effectiveness of blocking human mitochondrial DNA amplification. Assassin Blocker oligonucleotide sequences also terminated in TATA or ATAT at the 3' end to facilitate cross-linking (see Example 2, below).

Calculating Human Mitochondrial Sequence Relative Incidence

The preference of a given oligonucleotide for binding to a human mitochondrial DNA sequence to be blocked from amplification can be quantified in terms of the relative incidence of the complementary sequence in the mitochondrial genome (first population) compared to a microbial genome (second population). In this calculation, all possible oligonucleotides in the human mitochondrial genome which comprise 23 nucleotide bases (23mers) that terminate in TATA or ATAT are analyzed. The last 8 nucleotides (8mer) at the 3' end of the 23mer are used in the analysis. The 23 nucleotide sequence is unique to the mammalian mitochondrial DNA genome relative to the microbial DNA genome. The 8 nucleotide sequence is less frequent in the microbial DNA genome with respect to the mammalian mitochondrial DNA genome. The human mitochondrial sequence preference or relative incidence for a given blocking oligonucleotide is calculated using the following formula:

Relative Incidence=[(number of times the 8mer appears in a human mitochondrial genome)/(length of the human mitochondrial genome)]/[(number of times the 8mer appears in reference bacterial genome)/(length of reference bacterial genome)]

In this Example, the specific genome was human mitochondrial DNA (first population). The relative incidences were sorted from highest to lowest values, and unique oligonucleotide sequences with human mitochondrial relative incidence values greater than 2 were selected. Sets of oligonucleotide sequences which were complementary to sequences distributed every 2 kilobases in the human mitochondrial genome were utilized for further studies. Exemplary Assassin Blocker oligonucleotide sequences are listed in Table 1.

| 23mer sequence (3'→5') | SEQ ID NO: | Mitochondrial location | 8mer average mitochondrial relative incidence | 8mer median mitochondrial relative incidence |
|---|---|---|---|---|
| TATAGGCGATAGAAATTGAAACC | 1 | 1743 | 11.6 | 10.1 |
| TATACCCTTCCCGTACTAATTAA | 2 | 4452 | 7.24 | 6.4 |
| TATACTAATAATCCTTATAGAAAT | 3 | 5495 | 25.18 | 8.0 |
| TATACTACTAACAGACCGCAACC | 4 | 6524 | 31.5 | 16 |
| TATACTACGGTCAATGCTCTGAA | 5 | 8157 | 31.5 | 16 |
| TATACTAGCATTTACCATCTCAC | 6 | 10493 | 40.3 | 9.1 |
| TATAGCACTCGAATAATTCTTCT | 7 | 13600 | 10.4 | 8.4 |
| TATACCCTAGCCAACCCCTTAAA | 8 | 15512 | 7.24 | 6.4 |
| 23mer sequence (5'→3') | | Mitochondrial location | 8mer average mitochondrial relative incidence | 8mer average mitochondrial relative incidence |
| CACCACCTCTTGCTCAGCCTATA | 9 | 1236 | 13.9 | 12.8 |
| ATAGAAGAACTAATGTTAGTATA | 10 | 2286 | 25.2 | 8.0 |
| CTAATAATCGGTGCCCCCGATAT | 11 | 6156 | 7.0 | 4.0 |
| CACACATTCGAAGAACCCGTATA | 12 | 7410 | 10.5 | 10.1 |
| ATAGGGCCCGTATTTACCCTATA | 13 | 8426 | 28.1 | 25.1 |
| TCACTTCTAGGAATACTAGTATA | 14 | 10512 | 40.3 | 9.1 |
| TACCTCCCTGACAAGCGCCTATA | 15 | 13581 | 11.6 | 10.1 |
| AATGGGCCTGTCCTTGTAGTATA | 16 | 15879 | 31.5 | 16.0 |

>SEQ ID NO: 17 (reverse complement of SEQ ID NO: 1)
GGTTTCAATTTCTATCGCCTATA
>SEQ ID NO: 18 (reverse complement of SEQ ID NO: 2)
TTAATTAGTACGGGAAGGGTATA

```
>SEQ ID NO: 19 (reverse complement of SEQ ID NO: 3)
ATTTCTATAAGGATTATTAGTATA
>SEQ ID NO: 20 (reverse complement of SEQ ID NO: 4)
GGTTGCGGTCTGTTAGTAGTATA
>SEQ ID NO: 21 (reverse complement of SEQ ID NO: 5)
TTCAGAGCATTGACCGTAGTATA
>SEQ ID NO: 22 (reverse complement of SEQ ID NO: 6)
GTGAGATGGTAAATGCTAGTATA
>SEQ ID NO: 23 (reverse complement of SEQ ID NO: 7)
AGAAGAATTATTCGAGTGCTATA
>SEQ ID NO: 24 (reverse complement of SEQ ID NO: 8)
TTTAAGGGGTTGGCTAGGGTATA
>SEQ ID NO: 25 (reverse complement of SEQ ID NO: 9)
CACCACCTCTTGCTCAGCCTATA
>SEQ ID NO: 26 (reverse complement of SEQ ID NO: 10)
TATACTAACATTAGTTCTTCTAT
>SEQ ID NO: 27 (reverse complement of SEQ ID NO: 11)
ATATCGGGGGCACCGATTATTAG
>SEQ ID NO: 28 (reverse complement of SEQ ID NO: 12)
TATACGGGTTCTTCGAATGTGTG
>SEQ ID NO: 29 (reverse complement of SEQ ID NO: 13)
TATAGGGTAAATACGGGCCCTAT
>SEQ ID NO: 30 (reverse complement of SEQ ID NO: 14)
TATACTAGTATTCCTAGAAGTGA
>SEQ ID NO: 31 (reverse complement of SEQ ID NO: 15)
TATAGGCGCTTGTCAGGGAGGTA
>SEQ ID NO: 32 (reverse complement of SEQ ID NO: 16)
TATACTACAAGGACAGGCCCATT
```

Example 2

Cross-linking of Assassin Blockers to Complementary Sequences

Figure 1:
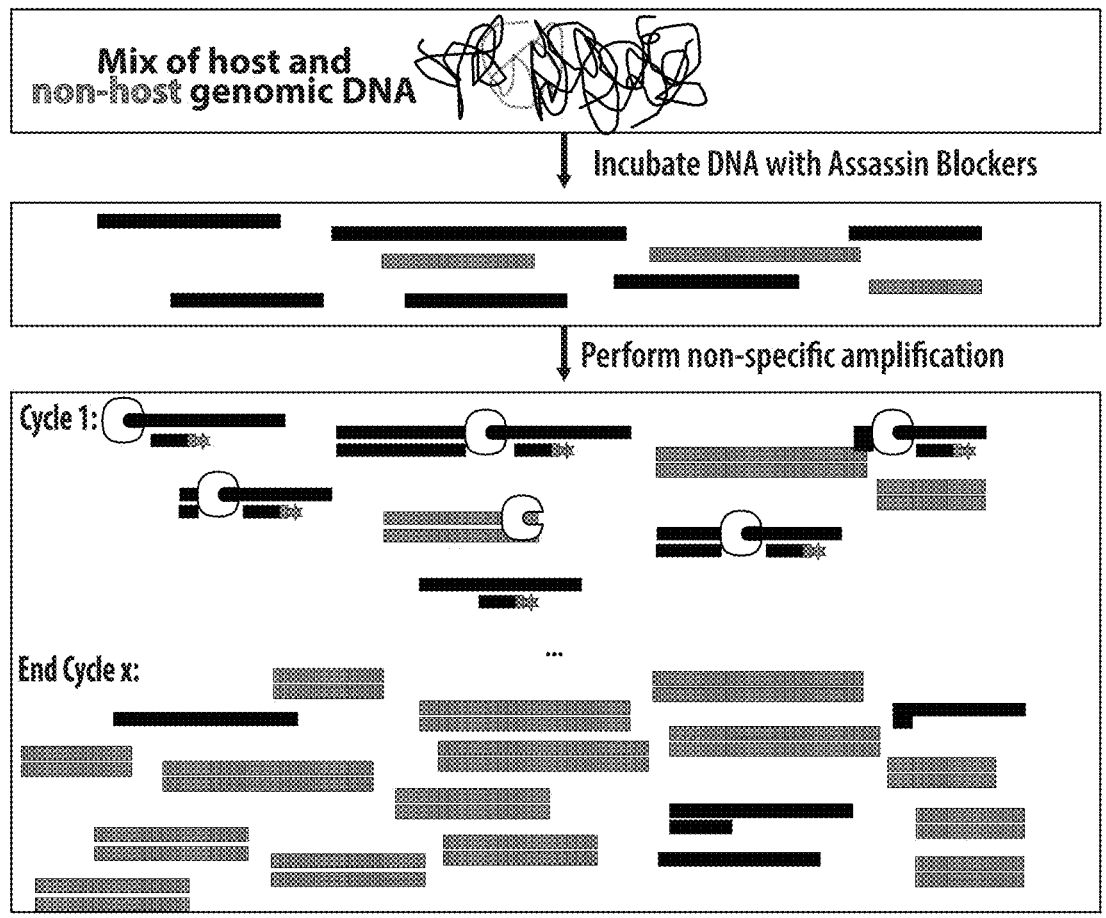
FIG. 1 shows the application of Assassin Blocker DNA oligonucleotides to the amplification reaction. A sample comprising a mixture of host (e.g., nuclear and human mitochondrial) and non-host (e.g., microbial) DNA is fragmented into fragments ranging from 1-100 kb in size. The host and non-host DNA fragments are incubated with one or more Assassin Blocker DNA oligonucleotides which bind selectively to a subset of the host DNA fragments. The Assassin Blocker oligonucleotide is then cross-linked to the subset of host DNA fragments through UV activation. Non-specific PCR amplification of the host and non-host DNA is then performed using a strand-displacing polymerase. The Assassin Blocker DNA oligonucleotides block the activity of the strand-displacing polymerase, thereby blocking the amplification of the subset of host DNA bound by Assassin Blocker oligonucleotides. The result of the non-specific PCR is a mixture that is enriched for non-host DNA.
Figure 2:
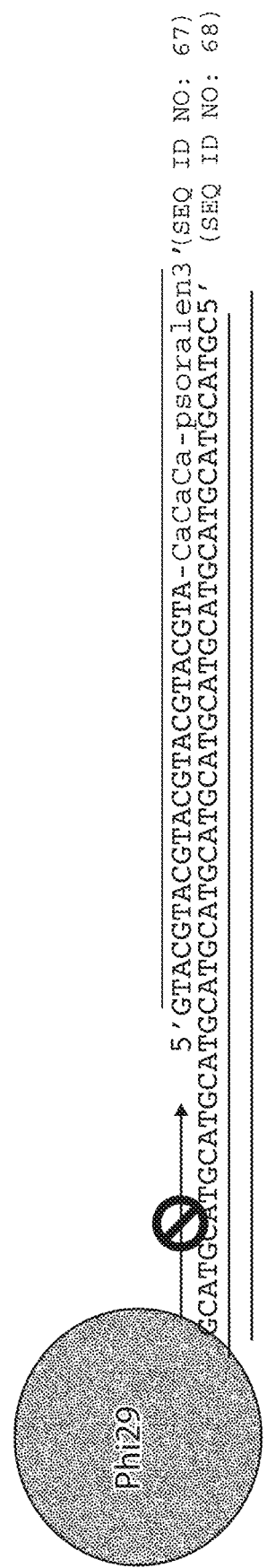
FIG. 2 is an illustration of an Assassin Blocker DNA oligonucleotide (top strand) bound to host (e.g., human mitochondrial) DNA (bottom strand). The Assassin Blocker oligonucleotide is modified at the 3' end with a spacer followed by a psoralen group. The psoralen group forms an interstrand cross-link to host DNA in the presence of UV irradiation. This interstrand cross-link blocks the procession of a strand-displacing polymerase, such as phi29.

The amplification of the first population of DNA can be blocked by cross-linking the Assassin Blocker oligonucleotide designed in Example 1 to its complementary sequence in the first population of human mitochondrial DNA. This cross-linking blocks whole genome amplification of the sequence by a strand-displacing polymerase such as phi29 (FIG. 2).

Lyophilized Assassin Blocker oligonucleotides with a modified 3' amino group were designed as in Example 1 and purchased (Integrated DNA Technologies, Coralville, Iowa). The lyophilized oligonucleotide was resuspended in phosphate buffered saline (1×PBS) and conjugated with a NHS-SPB (succinimidyl-[4-(psoralen-8-yloxy)]-butyrate, "psoralen") molecule (ThermoFisher, Waltham, MA). The conjugation reaction was quenched with Tris-HCl and excess psoralen is removed with a desalting column (ThermoFisher, Waltham, MA). The conjugated psoralen group is activated via UVA treatment to create interstrand cross-links between the Assassin Blocker oligonucleotide and the complementary human mitochondrial DNA sequence.

Example 3

Figure 3:
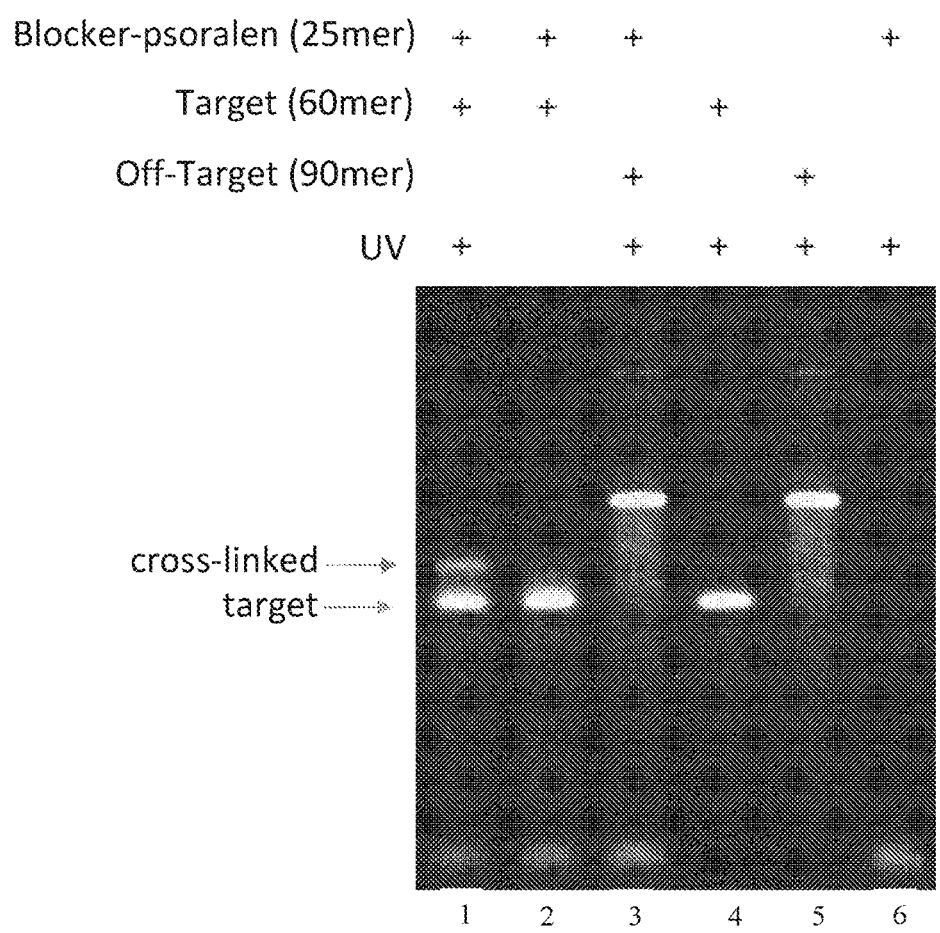
FIG. 3 shows the effects of cross-linking an Assassin Blocker oligonucleotide to a target oligonucleotide using a 25 nucleotide (25mer) oligonucleotide which was complementary to a 60 nucleotide (60mer) target oligonucleotide. A 90mer off-target oligonucleotide was used in Lanes 3 and 5 as a negative control to assess non-specific binding of the Assassin Blocker. Lane 1 is a sample comprise a 25mer Assassin Blocker oligonucleotide and a 60mer target oligonucleotide that was exposed to UV light; lane 2 is a sample comprising a 25mer Assassin Blocker oligonucleotide and a 60mer target oligonucleotide that was not exposed to UV light; lane 3 is a sample comprising a 25mer Assassin Blocker oligonucleotide and a 90mer off-target oligonucleotide that was exposed to UV light; lane 4 is a sample comprising a 60mer target oligonucleotide that was exposed to UV light; lane 5 is a 90mer off-target oligonucleotide that was exposed to UV light. The stable interaction of an Assassin Blocker oligonucleotide with a target oligonucleotide requires UV light to form a cross-link (lanes 1 vs. 2). A cross-linked Assassin Blocker oligonucleotide:target oligonucleotide complex migrates more slowly through the gel than either the Assassin Blocker oligonucleotide or target oligonucleotide alone (lane 1 vs. lanes 4 and 6). The Assassin Blocker oligonucleotide binds specifically to the target oligonucleotide and not the off-target oligonucleotide (lanes 3 vs. 5).

Demonstration of Sequence-Specific Covalent Cross-Linking of an Assassin Blocker to Target DNA To demonstrate the sequence-specific covalent cross-linking of Assassin Blocker oligonucleotides to target DNA, a reaction mixture of various Assassin Blocker oligonucleotides with psoralen conjugated to the 3' end, target oligonucleotides, and off-target oligonucleotides were added to an annealing buffer consisting of 40 mM Tris HCl (pH 7.9), 50 mM NaCl, and 10 mM MgCl$_2$ at 0.5 µM. The reaction mixture was heated to 94° C. for 5 minutes and cooled to 16° C. over 15 minutes. The reaction mixture was then treated with 350 nm ultra-violet (UV) light for 20 minutes. The reaction mixture products were separated on a 10% Tris-Borate-EDTA (TBE)-urea gel in 1×TBE buffer. The gel was stained with SYBR-gold (ThermoFisher, Waltham, MA) and visualized on an E-gel Imager (ThermoFisher, Waltham, MA). (FIG. 3).

Figure 5:
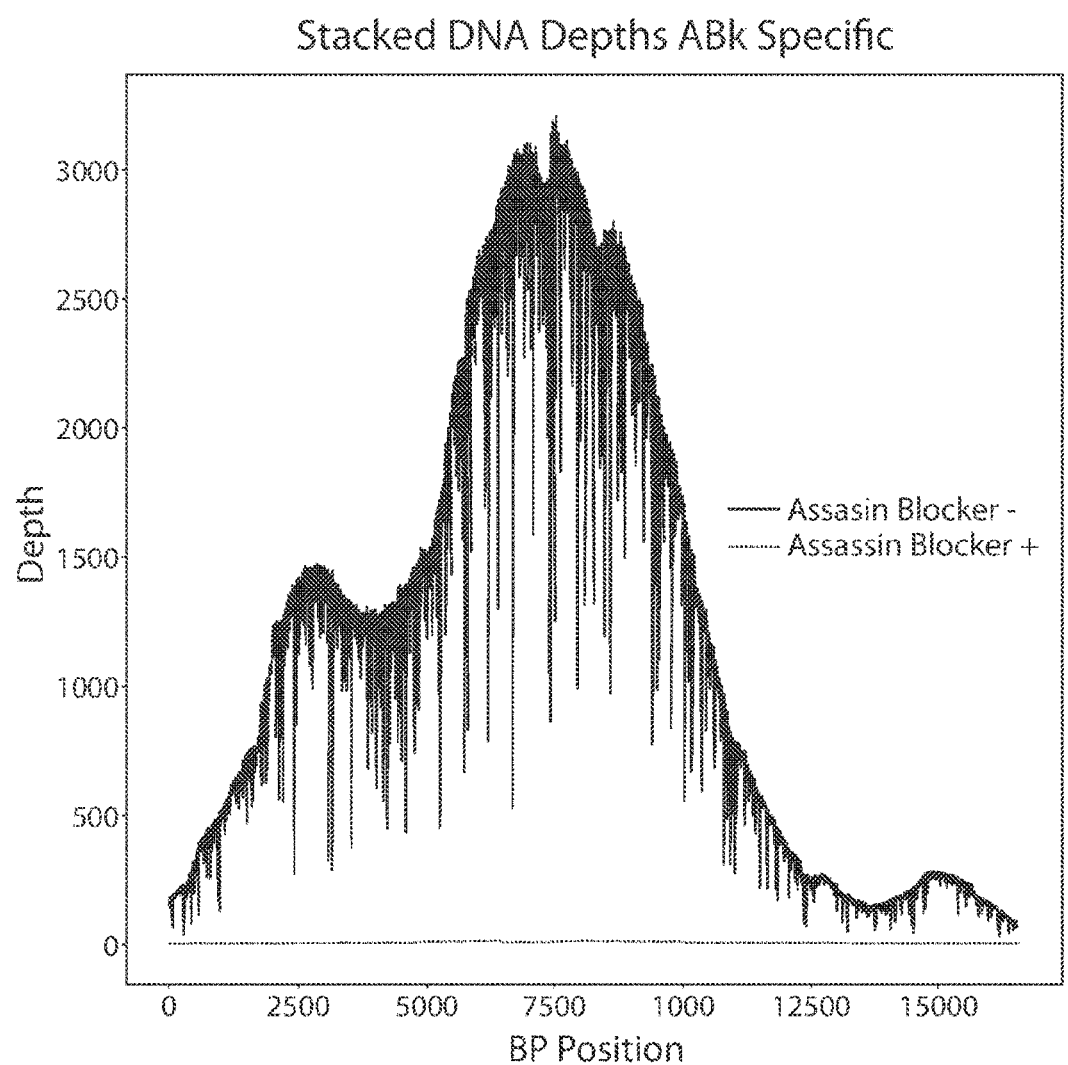
FIG. 5 shows the numbers of reads (depths of reads) across 16,569 base pairs of mammalian mitochondrial DNA sequences from samples treated with Assassin Blocker oligonucleotides (black) or samples not treated with Assassin Blocker oligonucleotides (gray).

The reduction of human mitochondrial DNA was demonstrated from a mixed sample comprising human nuclear and mitochondrial DNA along with microbial DNA derived from E. coli (FIG. 5). The cells in the mixed sample were lysed with an alkaline lysis buffer as described by the REPLI-g Single Cell kit (Qiagen, Hilden, Germany) and then heated to 65° C. 1 µL of Assassin Blocker oligonucleotides were added at a 1 µM concentration (Assassin Blockers +) targeting the human mitochondrial DNA or TBE buffer (Assassin Blockers –) were added to the lysed sample and treated with 350 nm UV light for 20 minutes. The samples were amplified as described by the REPLI-g Single Cell kit (Qiagen, Hilden, Germany) and sequenced by MinION sequencing (Oxford Nanopore Technologies, Oxford, United Kingdom). Reads from both the Assassin Blocker + and Assassin Blockers – samples were mapped to the human mitochondrial DNA and the depth of human mitochondrial reads are displayed graphically.

As shown in FIG. 5, treatment with Assassin Blockers oligonucleotides results in significant reduction in sequencing reads across the entire human mitochondrial genome from a mixed sample comprising human nuclear, human mitochondrial, and E. coli nucleic acids.

Example 4

Assassin Blocker Oligonucleotides Reduce Human Mitochondrial DNA Amplification

The reduction of human mitochondrial DNA amplification in a mixed sample comprising human nucleic acid populations and bacterial nucleic acid populations through the use of Assassin Blocker oligonucleotides was examined.

Figure 4:
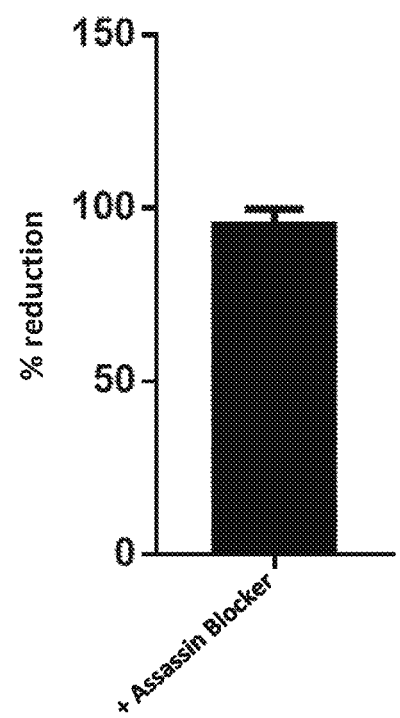
FIG. 4 shows the reduction of host (e.g., human mitochondrial) DNA when Assassin Blocker oligonucleotides are utilized. The percent reduction is normalized to host DNA when Assassin Blocker oligonucleotides are not utilized.

Clinical blood samples (n=4) from human subjects were spiked with bacteria (e.g., *Escherichia coli, Staphylococcus aureus*, or *Klebsiella pneumoniae*) at either 100 colony forming units/milliliter (100 CFU/mL) or 10 CFU/mL. The use of Assassin Blocking oligonucleotides when activated by UV light resulted in greater than 90% reduction of human mitochondrial DNA sequenced as a percentage of total reads compared to control samples which were not cross-linked with UV light (FIG. 4). The percent reduction of human mitochondrial DNA amplification when Assassin Blocker oligonucleotides were cross-linked to complementary human mitochondrial sequences was greater than 90% compared to control samples where Assassin Blocker oligonucleotides were not cross-linked.

Example 5

Method to Manufacture Winged Blocker DNA Oligonucleotides

The following steps were used to generate Winged Blocker oligonucleotides that block the entire genome of a species whose amplification is undesirable, exemplified here (FIG. 6):
1.) Digest concentrated host (e.g., mammalian mitochondrial) genomic DNA (gDNA) using two restriction enzymes with different 4-mer cutting activity (e.g., MspI and MseI).
2.) Remove digested gDNA fragments smaller than 100 bp.
3.) Ligate Winged Blocker oligonucleotides, which are designed to complement the blunt overhangs created by the restriction enzymes, to the digested gDNA fragments using a ligase.
4.) PCR amplify the primer-ligated host gDNA using custom designed primers, where the 5' end of the forward primer is phosphorylated, and the 5' end of the reverse primer is biotinylated (or contains another bulk modification to prevent lambda exonuclease digestion).
5.) Digest the primer-adapted host DNA to degrade the 5' phosphorylated strand using a lambda exonuclease.

This results in a library of single-stranded blockers containing a portion of host gDNA that is flanked by 20-50 base pair "wings" (regions of non-complementarity to the host gDNA) on both the 5' and 3' ends. These blockers span the entire host genome.

The host genome was purified from a host cell utilizing phenol:chloroform:isoamyl alcohol precipitation, but any method known in the art can be utilized. Ideally, the DNA is extracted in a manner that retains high-molecular weight chromosomal fragments and avoids excessive shearing which generates DNA fragments smaller than 5,000 base pairs. Next, the DNA is digested using a double restriction enzyme digest with MspI (R0106S, New England Biolabs, Ipswich, MA) and MseI (R0525L, New England Biolabs, Ipswich, MA). For example, 0.5 µg of genomic DNA is mixed with 5 µL of 10× optimized buffer and 38.5 µL of DNA-free and nuclease free water. To this mixture, 0.5 µL of MspI and 1 µL of MseI restriction enzyme is added and pipetted to mix. After incubating for 5-15 minutes at 37° C., the restriction enzymes and resulting fragments below base pairs in length are removed from the digested genomic DNA using a size exclusion spin column. Filter-based columns should not be used, as they result in significant loss of digested DNA product.

Individually, the GC-terminus adapter and AT-terminus adapter are made by mixing equal volumes of the short and long primers together at 100 µM concentration and incubating for 10 minutes at room temperature. 1 µL of digested DNA at 0.02 pmol is mixed with 1 µL of the GC-terminus adapter at 0.5 pmol, 1 µL of the AT-terminus adapter at 0.5 pmol, 2 µL of water, and 5 µL of a 2× Instant Sticky-end Ligase Master Mix (M0370, New England Biolabs, Ipswich, MA). After mixing 10 times by pipetting, the end-adapted fragmented genomic DNA is placed on ice and cleaned again with a size exclusion spin column. If a double-winged product is desired, the cleaned product is then PCR amplified using the P1 and P2 primers, for 30-35 cycles with an annealing temperature of 66° C. and the un-incorporated primers are removed with a size exclusion spin column. If a single-winged product is desired, the cleaned product is PCR amplified using the P1 primer in combination with a specially designed primer that binds to a specific sequence that has been computationally determined to lie within an enzymatically-cleaved fragment, preferably designed to maximize the length of the PCR product.

Exemplary Adaptor Sequences:

```
                                          (SEQ ID NO: 55)
LongAdapter_GC:
/5Phos/CGCTTAGCGACGTTCTGTCCCTCTGACCACATACG (SEQ ID NO: 56)
ShortAdapter_GC:
CGTCGCTAAG (SEQ ID NO: 57)
LongAdapter_AT:
AAGCACCATCTAGGTGTAGCCTGATGCCAGAT (SEQ ID NO: 58)
ShortAdapter_AT :
/5Phos/TAATCTGGCATCA
```

It is important to note that there is nothing special about these adaptor sequences, other than their h-shape. One of skill in the art will recognize that any h-shaped adaptor sequences, analogous to those described here, may be used according to the methods of the invention.

Exemplary Amplification Primer Sequences:

```
                                          (SEQ ID NO: 59)
    P1: 5'-CGTATGTGGTCAGAGGGACAGAA-3'

(SEQ ID NO: 60)
    P2: 5'-AAGCACCATCTAGGTGTAGCCT-3'
```

Alternative Exemplary Primer Sequences Include:

```
                                          (SEQ ID NO: 61)
Long adapter GC:
5'-CGTCTCGCCTTCGGACTGTTAGCACGGCCAGA 3'

(SEQ ID NO: 62)
Short adapter GC:
5'-GAAGGCGAGA-3'

(SEQ ID NO: 63)
Short adapter AT:
5'-TAGCATACGTGC-3'

(SEQ ID NO: 64)
Long adapter AT:
5'-GGTGCAGAGAACGAGACCTGGGCACGTATGC-3'rev (SEQ ID NO: 65)
P1:
5'-5 TCTGGCCGTGCTAACAGTCC-3'
```

```
                                        (SEQ ID NO: 66)
P2:
   5'-GGTGCAGAGAACGAGACCTGG-3'
```

The double-stranded PCR product produced must then be converted into a single stranded product. The single-stranded product is the blocker that binds to the complementary over-represented DNA strands. The conversion of double-stranded into single-stranded DNA can be achieved using a number of processes, including but not limited to asymmetric PCR to selectively amplify the desired strand, lambda exonuclease digestion of the undesired strand, streptavidin bead separation of the strands, and in vitro transcription (Murgha et al., PLoS One, 2014). The first three methods are described here.

A) Amplification Primer Sequences if Using Asymmetric PCR

Figure 6:
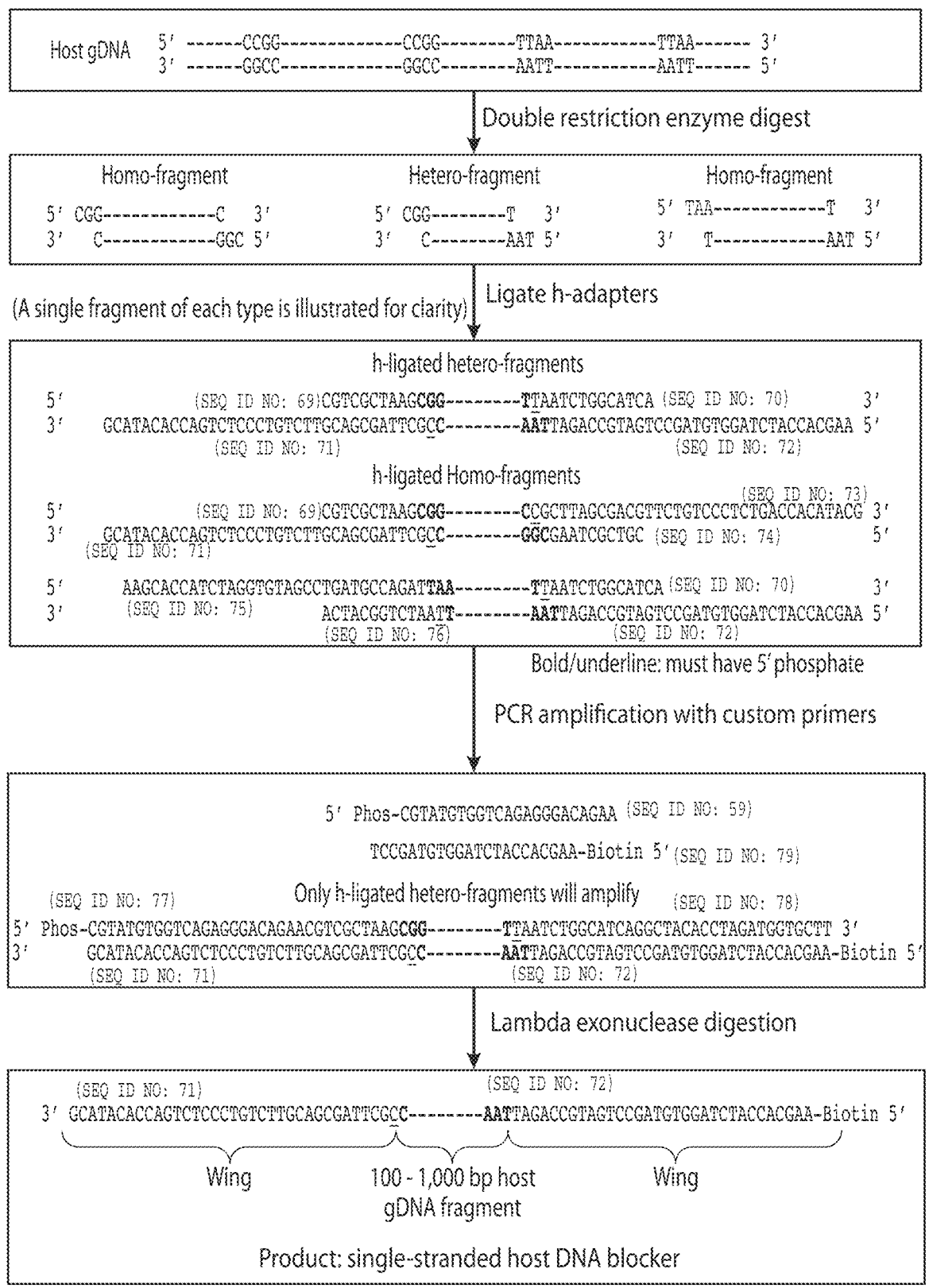
FIG. 6 is the manufacturing process for winged host DNA blocking. Stage 1: double-stranded host DNA with locations of two different palindromic restriction sites, Site X and Y, distributed throughout the genome. Stage 2: the host genomic DNA is broken into fragments using a double restriction enzyme digest. Some fragments have the X site at both ends and some fragments have the Y site at both ends, in each case referred to herein as "homo fragments". In contrast, some fragments have an X site at one end and a Y site at the other end, herein referred to as "hetero fragments".

Asymmetric PCR uses an unequal concentration of primers to favor the amplification of a single strand. The PCR reaction described in Step 4 of this example where the blocker is amplified using the P1 and P2 primers as shown in FIG. 6 step 4, is modified such that the ratio of P1:P2 primer input is 1:10 to 1:50. The number of PCR cycles must be decreased to 15-20 cycles to avoid non-specific amplification. The resulting asymmetric PCR product is purified using the same size exclusion spin column that eliminates fragments smaller than 20 base pairs in length.

B) Amplification Primer Sequences if Using Lambda Exonuclease Digestion

An alternative approach uses the lambda exonuclease enzyme to preferentially degrade the undesired DNA strand. Lambda exonuclease has a preferred substrate of 5'-phosphorylated double stranded DNA and acts in the 5' to 3' direction. Its highly processivity ensures that an entire strand is degraded within a DNA fragment. To prepare double-stranded DNA that is suitable for lambda exonuclease digestion, the P1 amplification primer must be modified with a 5' phosphate group, which can be obtained from a commercial manufacturer such as Integrated DNA Technologies, Inc. (Coralville, IA). The 5'-phosphorylated P1 amplification primer is then used in the PCR reaction described in conjunction with the unphosphorylated P2 amplification primer. After 30-35 cycles of amplification and a size-based column purification, 3 µL of the purified product is incubated with 0.5 µL of lambda exonuclease (M0262, New England Biolabs, Ipswich, MA), 1 µL of 10× exonuclease I buffer, and 5.5 µL of DNA and nuclease-free water for 60 minutes at 37° C. The product is cleaned up with a size-exclusion column (e.g. CentriSpin 20, Princeton Separations, Inc., Freehold, NJ) and can hereon be used as a Winged Blocker probe.

C) Amplification Primer Sequences if Using Streptavidin Bead Separation

The following steps use streptavidin-coated magnetic beads (e.g. Dynabeads™ MyOne™ Streptavidin C1, ThermoFisher, Waltham, MA) to separate the desired blocker from its complementary strand. To prepare double-stranded DNA that is suitable for streptavidin bead separation, the P1 amplification primer must be modified with a 5' biotin group, which can be obtained from a commercial manufacturer such as Integrated DNA Technologies, Inc. (Coralville, IA). The 5'-biotinylated P1 amplification primer is then used in the PCR reaction shown in FIG. 6, step 4 and described in Example 5, step 4 in conjunction with the unbiotinylated P2 amplification primer, followed by 30-35 cycles of amplification and size-based column purification. The magnetic beads are washed per manufacturer's instructions and the PCR amplification product is then incubated for 15-30 minutes with the washed beads at room temperature with gentle agitation. The bead-DNA mixture is then placed in a magnet for 2-3 minutes, the supernatant is discarded, and the beads are washed 3-4 times in washing buffer. The desired blocker strand is then denatured from the complementary strand that is bound to the magnetic bead by two serial incubations of 50 µL of the bead-DNA mixture with 40 µL of 0.125 M sodium hydroxide for two minutes at room temperature (Murgha et al., PLoS One, 2014). The supernatant of the washes (about 80 µL in total) is combined and neutralized with 12 µL of 1 M HCl and 8 µL of 1 M Tris-HCl pH 8. The product is cleaned up with a size-exclusion column (e.g., CentriSpin 20, Princeton Separations, Inc., Freehold, NJ) and can hereon be used as a blocker probe.

Example 6

Method for Making Single-Stranded Winged Blockers Using H-Adapters

Here we describe a method of making single-stranded blockers with wings to block extension by a polymerase from human genomic DNA. First, deterministic fragments of human DNA are produced by digesting DNA extracted from human cells with two restriction enzymes that digest a different palindromic site with an overhang. The sites are referred to herein as 'Site A' and 'Site B'. We then incubate with 'h-adapters' and DNA ligase. There are two h-adapters, A and B, matching Site A and Site B, respectively. The h-adapters each comprise a pair of complementary oligonucleotides that contain, e.g., 6-30 nucleotides. One strand of the pair is longer than the other. The A h-adapter ligates to the A restriction site and the B h-adapter ligates to the B adapter. The mixture is then amplified using one PCR primer complementary to the long A adapter strand (primer A), and one primer in the same orientation as is the B adapter strand (primer B). Only fragments that contain one of each restriction site are capable of being amplified. After amplification, each double-stranded amplicon has exactly one strand containing primer A and one strand containing primer B, on the 5' end in each case. These can be used to preferentially pull down or destroy one strand or the other, leaving single-stranded DNA. For example, a 5' phosphate group may be added to primer A, and the amplicons digested with an enzyme that destroys phosphorylated DNA. This process is shown schematically in FIG. 6. Alternatively, if one performs only a single restriction digest, it would yield fragments with symmetry that makes the two strands indistinguishable based on their ends alone. Similarly, if one performs a double-digest, but then ligates with full double-stranded adapters, the resulting fragments would be distinguishable, but PCR would produce amplification of all three combinations (see FIG. 6).

Example 7

Methods to Use Winged Blockers to Prevent Amplification of an Over-Represented Population's Nucleic Acid The following steps were used to apply Winged Blockers to prevent amplification of the over-represented population's genomic nucleic acid, exemplified for the case of DNA blockers (FIG. 7):

1. Fragment the mixture of genomic DNA from the over-represented and under-represented populations into fragments between 1,000 to 15,000 base pairs.
2. Incubate fragmented gDNA with the over-represented population's DNA blockers, manufactured in Example 5, for 5 minutes to overnight at room temperature to 70° C.
3. Perform PCR amplification using the fragmented gDNA, random hexamer primers, and a high-fidelity polymerase that is optimized for long amplicons (e.g. LongAmp Taq, New England Biolabs, Ipswich, MA).

The PCR reaction can be performed with any non-strand-displacing polymerase. For example, when using the Phusion High Fidelity polymerase (M0530, New England Biolabs, Ipswich, MA) with a 25 µL reaction volume, the master mix contains 5 µL of 5× Phusion High Fidelity Buffer (New England Biolabs, Ipswich, MA), 0.5 µL dNTPs at 10 mM, 0.75 µL DMSO, and 0.25 µL Phusion polymerase (New England Biolabs, Ipswich, MA). The 6.5 µL of Master Mix (New England Biolabs, Ipswich, MA) can be combined with the mixed genomic DNA solution and the single stranded blockers. For example, FIG. 8 was produced by combining 6.5 µL master mix, 1 µL of E. coli DNA at 1 ng/µL (equivalent to approximately 200,000 E. coli genome copies), 1 µL of M13mp18 RF I bacteriophage DNA (New England Biolabs, Ipswich, MA) at 0.05 ng/µL (equivalent to approximately 6.5 million genomes copies), with or without the forward and reverse primers specific for the bacterial 16S ribosomal RNA gene sequence, and the forward and reverse primers specific for the M13 bacteriophage genome. The reaction volume was brought up to 25 µL with the single-stranded M13 bacteriophage blocker produced by Example 5. The mixture was subjected to PCR amplification using a slightly modified PCR amplification procedure. The first modification was only 20 cycles of amplification performed to ensure that the M13 bacteriophage blocker concentration was sufficient to provide adequate blocking even after exponential amplification of the gene regions of interest. The second modification was that the extension temperature was decreased to 68° C. to optimize the thermodynamic stability of the blocker amplicon hybridization without compromising the processivity of the polymerase. The PCR program used an initial denaturation at 98° C. for 30 seconds, followed by 20 cycles of denaturation at 98° C. for 10 seconds, annealing at 65° C. for 20 seconds, extension at 68° C. for 30 seconds, and a final extension at 72° C. for 10 minutes. The products were then run on a 1.2% agarose gel and quantified using ImageJ software.

Example 8

Application of Winged Blockers to Suppress M13 Phage DNA in the Presence of E. coli Genomic DNA In a proof of concept experiment, we blocked the amplification of a segment of the M13 phage DNA genome in the presence of E. coli DNA using our manufactured blockers against the M13 phage (FIG. 8). The blocking probes in this case were made using the process described in Example 5 (see also FIGS. 6 and 7), except that these blockers have only a single wing, on the 3' end, instead of the double wing described in Example 5. This experiment shows that the single wing blocker is able to decrease the amplification of the M13 amplicon in the presence of excess E. coli genomic DNA, demonstrated by decreased brightness of the M13 band relative to that of the bacterial 16S rRNA gene band which is left intact. E. coli and M13 phage DNA were contained in all wells. The fluorescence intensity in each region of a band was measured using ImageJ software.

Fluorescent intensity profiles of the M13 band and 16S band are shown in FIG. 9. The M13 band was quantified with M13 primers plus and minus blockers; and compared to reactions that had both M13 and 16S primers plus and minus blockers (where the blocker was manufactured with a single wing using universal amplification primer P1 and an M13-specific reverse primer 387R). Average background fluorescence intensities across the gel were subtracted to calculate a corrected average intensity for each band. The decrease in M13 amplicon amplification in the presence of the M13 blocker was 42-68%, with lower efficiency in the presence of E. coli amplicon amplification that was presumably due to competition for PCR resources. The decrease in E. coli amplicon amplification in the presence of the M13 blocker was 13% (FIG. 9), which is again also likely due to competition for PCR resources.

Example 9

Designing Assassin Blockers or Winged Blockers Against Lactobacillus Crispatus to Enrich for Chlamydia trachomatis in a Mixed Microbial DNA Sample Female genital tract samples are often predominantly comprised of Lactobacillus species, most often Lactobacillus crispatus, and genital pathogens, such as Chlamydia trachomatis, Neisseria gonorrhoeae, Trichomonas vaginalis, HSV-2, or HIV, are generally found at much lower abundances than the native vaginal bacterial flora. In cases where one is interested in sequencing the genome of a pathogen from a genital specimen, such as a vaginal swab, for pathogen identification and characterization purposes, the sensitivity of the sequencing result for the pathogen's genome can be increased by selectively suppressing the amplification of lactobacilli, e.g. Lactobacillus crispatus through the use of Assassin Blockers or Winged Blockers.

Table 2 lists Assassin Blockers that are unique 23mers and are also more frequent in Lactobacillus crispatus as 8mers when compared to a potential infectious organism of interest, Chlamydia trachomatis. Table 2 lists Assassin Blocker oligonucleotides for the first 20 kb of the L. crispatus genome, but Assassin Blocker oligonucleotide sequences will also be identified for the remainder of the 2,000,000 base pair genome. These Assassin Blockers will be applied to DNA extracted from a genital specimen, such as a vaginal swab, as detailed in Examples 2 and 3 to suppress the amplification of the predominant organism, L. crispatus, and allow deeper sequencing of the C. trachomatis genome. Using Assassin Blockers against L. crispatus, the ratio of sequencing reads from C. trachomatis to L. crispatus will increase from 1:1000 to 1:10 or even 1:1, thereby enabling excellent coverage of the C. trachomatis genome with standard next-generation sequencing methods (e.g. 1 million reads per sample, and 150 base pair, paired-end reads.)

| 23mer sequence (3'→5') | SEQ ID NO: | L. crispatus location | 8mer L. crispatus relative incidence |
|---|---|---|---|
| TATAATTACTAATAAAGAAAAAT | 33 | 1492 | 4.28 |
| TATAATTATATAGGTATAAAGCG | 34 | 2864 | 4.28 |
| TATAATTATATAGGTATAAAGCG | 35 | 4099 | 4.28 |

-continued

| 23mer sequence (5'→3') | SEQ ID NO | L. crispatus location | 8mer L. crispatus relative incidence |
|---|---|---|---|
| ATATTACTTGGATCACCAAGAAG | 36 | 7282 | 3.61 |
| ATATTACTGAAAAGAATGGTCCT | 37 | 8451 | 3.61 |
| ATATTAATGGTAATGATAGAGCA | 38 | 10808 | 3.35 |
| ATATATTAAATCCTATAATTTGG | 39 | 12146 | 4.26 |
| TATACTAATGTTCATGCCAAATT | 40 | 15441 | 2.95 |
| ATATAATACGAATAATATTTACA | 41 | 16962 | 4.16 |
| TATAATATATCAGTTAAAATAGA | 42 | 18087 | 4.76 |
| TATAATATATCAGTTAAAATAGA | 43 | 20143 | 3.61 |

| 23mer sequence (5'→3') | | L. crispatus location | 8mer L. crispatus relative incidence |
|---|---|---|---|
| CCTACTACTACTAATTAATTATA | 44 | 1471 | 4.28 |
| GGTTGAAAACTAATATAATTATA | 45 | 2851 | 4.28 |
| CAAAGTGCGCTACTTAATTATAT | 46 | 4100 | 3.31 |
| GTTGTTCGCGCCAAAACCAATAT | 47 | 6950 | 2.37 |
| AAATTAGAAATTGCGAGTAATAT | 48 | 8833 | 3.61 |
| CAAGATAACACACAATACTTATA | 49 | 11984 | 6.02 |
| AAAATAATTTAGGCGTAATATAT | 50 | 13514 | 4.26 |
| AAAGAAGCTACTAAGGGTAATAT | 51 | 15168 | 3.47 |
| GCGATTAATGATATTAATAATAT | 52 | 16036 | 3.28 |
| TTCTTTTTGTTTCTATATAATAT | 53 | 18072 | 4.76 |
| GATGGCAATCGTACCATCAATAT | 54 | 20622 | 3.17 |

Winged Blockers can also be manufactured against *Lactobacillus* crispatus. A purified culture of *Lactobacillus* crispatus will be lysed, the genomic DNA will be isolated and cleaned, and this genomic DNA will be used to manufacture L. crispatus Winged Blockers using the processed detailed in Example 5. The L. crispatus Winged Blockers will then be applied to DNA extracted from a genital specimen, such as a vaginal swab, as detailed in Example 7 to suppress the amplification of the predominant organism, L. crispatus, and allow deeper sequencing of the C. trachomatis genome.

While some embodiments of the invention have been described by way of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety.

REFERENCES

1. Martin, G. S., et al., "The Epidemiology of Sepsis in the United States from 1979 through 2000," *New England Journal of Medicine*, 2003, 348: 1546-1554.
2. Kvist, T., et al., "Specific single-cell isolation and genomic amplification of uncultured microorganisms," *Appl. Microbiol. Biotechnol.* 2007, 74(4): 926-935.
3. Huang, L., et al., "Single-Cell Whole-Genome Amplification and Sequencing: Methodology and Applications," *Annu Rev Genomics Hum Genet.*, 2015, 16: 79-102.
4. Boardman, A. K., et al., "Rapid Microbial Sample Preparation from Blood Using a Novel Concentration Device," *PLoS One*, 2015, 10(2): e0116837.
5. Kolodney, M. S., et al., "Selective Amplification of Minority Mutations Using Primer Blocking High-Affinity Oligonucleotides," US 2010/0009355, 2010.
6. Ecker, D. J., et al., "Targeted Whole Genome Amplification Method for Identification of Pathogens," US 2010/0035232, 2010.

What is claimed is:

1. An improved method for enrichment of a population of DNA by amplification of a mixed sample of DNA comprising a first population and a second population, the improvement comprising:
   (a) contacting the mixed sample of DNA with a plurality of blocking oligonucleotides which specifically bind to a plurality of oligonucleotide sequences in the first population of DNA; and
   (b) subjecting said mixed sample of DNA to whole genome amplification (WGA) to produce an amplified mixed sample of DNA;
   wherein said blocking oligonucleotides suppress amplification of the first population of DNA and thereby enrich the second population of DNA relative to the first population of DNA in the amplified mixed sample.

2. The method of claim 1 wherein:
   (a) each of the plurality of blocking oligonucleotides comprises a sequence of 6 to 50 nucleotides, wherein the complement of said sequence has a relative incidence in a genome of the first population of DNA relative to a genome of the second population of DNA of at least 50, 75, 100, 150, 200, or 250; and
   (b) each of the plurality of blocking oligonucleotides comprises a 3' sequence of at least 6-nucleotides, wherein the complement of said 3' sequence has a relative incidence in a genome of the first population of DNA relative to a genome of the second population of DNA of at least 2, 3, 4, 5, 6, 7, 8, 9, or 10.

3. The method of claim 1 wherein:
   each of the plurality of blocking oligonucleotides comprises a sequence of at least 6, 7, 8, 9 or 10 nucleotides, and/or fewer than 50, 45, 40, 35, 30 or 25 nucleotides, optionally wherein the 3' sequence of each of the plurality of the blocking oligonucleotides comprises at least 6, 7, 8, 9, 10, 11, 12, 13, 14 or 15 oligonucleotides, and/or fewer than 25, 20, 15, 14, 13, 12, 11 or 10 oligonucleotides.

4. The method of claim 1 wherein:
   the plurality of blocking oligonucleotides comprises at least 10, 20, 30, 40, 50, 75 or 100 different blocking oligonucleotides, or at least $10^3$, $10^4$, $10^5$, $10^6$, $10^7$ or $10^8$ different blocking oligonucleotides.

5. The method of claim 1 wherein:
   the maximum distance between the genomic sequences complementary to the first population of blocking oligonucleotides is 2G/N, 3G/N, 4G/N or 5G/N where G is the size of the genomic DNA corresponding to the first population and N is the number of different blocking oligonucleotides in the plurality of blocking oligonucleotides.

6. The method of claim 1 wherein:
   each of the plurality of blocking oligonucleotides further comprises an interstrand cross-linking agent that cross-links the blocking oligonucleotide to the first population of DNA, optionally wherein the cross-linking agent is photoactivated, optionally wherein the cross-linking agent is a psoralen.

7. The method of claim 1, wherein:
   each of the plurality of blocking oligonucleotides comprises a spacer at the 3' end which prevents a DNA polymerase from extending the oligonucleotide by template-dependent DNA synthesis, optionally wherein each spacer comprises an aliphatic molecule bound to the 3' OH of the corresponding blocking oligonucleotide.

8. The method of claim 7, wherein:
   each of the plurality of blocking oligonucleotides is a winged blocker, optionally wherein the winged blocker comprises a complementary oligonucleotide sequence of 40-60 nucleotides which is complementary to a sequence in the first population of DNA, optionally wherein:
   the winged blocker further comprises wing oligonucleotide sequences of 10-100 nucleotides at each end of the complementary nucleotide sequence, wherein the wing oligonucleotide sequences are not complementary to the flanking sequences in the first population of DNA.

9. The method of claim 1, wherein the WGA is performed using a strand-displacing polymerase, optionally wherein the WGA is performed using phi29 polymerase.

10. The method of claim 1 wherein:
the mixed sample is obtained or derived from blood, sputum, urine, mucus, saliva, tissue abscess, wound drainage, stool, lymph, lavage, cerebral-spinal fluid, or any fluid aspirate or tissue extraction of human and/or other eukaryotic origin, optionally wherein the mixed sample is obtained or derived from a human subject.

11. The method of claim 1 wherein:
(a) the first population comprises mammalian DNA, optionally wherein the mammalian DNA is human DNA; and/or
(b) the second population comprises microbial DNA, optionally wherein:
(i) the first population comprises a first type of microbial DNA and the second population comprises a second type of microbial DNA; or
(ii) the first population comprises mammalian DNA and the second population comprises microbial DNA and the ratio of mammalian DNA to microbial DNA is at least $10^2$, $10^3$, $10^4$, $10^5$, $10^6$, $10^7$ or $10^8$; or
(iii) the first population of DNA comprises mammalian mitochondrial DNA and the second population comprises microbial DNA.

12. The method of claim 11 wherein:
the microbial DNA comprises DNA from *Staphylococcus aureus, Staphylococcus epidermidis, Streptococcus agalactiae, Enterococcus faecalis, Enterococcus faecium, Escherichia coli, Klebsiella pneumoniae*, or any other bacterial species associated with bacteremia.

13. The method of claim 11, wherein the microbial DNA in the mixed sample corresponds to fewer than 10 microbial genomes, optionally wherein:
(i) the microbial DNA in the amplified sample is enriched by between 10-fold and 100-fold relative to the mixed sample; and/or
(ii) the mammalian DNA in the mixed sample is reduced by at least 50%, 60%, 70%, 80%, 90%, 95% or 99%.

14. The method of claim 1 wherein:
at least one of the plurality of blocking oligonucleotides is selected from SEQ ID NOs: 1-16, optionally wherein at least one of the plurality of blocking oligonucleotides binds to a sequence selected from SEQ ID NOs: 17-32.

15. A plurality of blocking oligonucleotides wherein:
(a) each blocking oligonucleotide comprises at least 6-25 consecutive nucleotides that are complementary to a genomic sequence, wherein the genomic sequence has a relative incidence within a genome of mammalian DNA compared to a genome of bacterial DNA of at least 2, 3, 4, 5, 6, 7, 8, 9 or 10; and
(b) each blocking oligonucleotide comprises at least one modified nucleotide that cross-links to a complementary genomic sequence;
wherein the maximum distance between genomic sequences complementary to multiple blocking oligonucleotides in the first population of blocking oligonucleotides is 2G/N, 3G/N, 4G/N or 5G/N where G is the size of the genomic DNA corresponding to the first population and N is the number of different blocking oligonucleotides in the plurality of blocking oligonucleotides.

16. The plurality of blocking oligonucleotides of claim 15, wherein:
(a) the genome of mammalian DNA is mammalian nuclear DNA or mammalian mitochondrial DNA; and/or
(b) the genome of bacterial DNA is genomic DNA selected from the group consisting of: *Staphylococcus aureus, Staphylococcus epidermidis, Streptococcus agalactiae, Enterococcus faecalis, Enterococcus faecium, Escherichia coli*, and *Klebsiella pneumoniae* genomic DNA.

17. The plurality of blocking oligonucleotides of claim 15, wherein each blocking oligonucleotide further comprises an interstrand cross-linking agent that cross-links the blocking oligonucleotide to the genomic sequence in the first population of DNA, optionally wherein the cross-linking agent is photoactivated, optionally wherein the cross-linking agent is a psoralen.

18. The plurality of blocking oligonucleotides of claim 15, wherein:
each of the plurality of blocking oligonucleotides further comprises a spacer at the 3' end which prevents a DNA polymerase from extending the oligonucleotide by template-dependent DNA synthesis, optionally wherein each spacer comprises an aliphatic molecule bound to the 3' OH of the corresponding blocking oligonucleotide.

19. The plurality of blocking oligonucleotides of claim 15, wherein:
each of the plurality of blocking oligonucleotides is a winged blocker, optionally wherein the winged blocker comprises a complementary oligonucleotide sequence of 40-60 nucleotides which is complementary to a sequence in the first population of DNA, optionally wherein:
the winged blocker further comprises wing oligonucleotide sequences of 10-100 nucleotides at each end of the complementary nucleotide sequence, wherein the wing oligonucleotide sequences are not complementary to the flanking sequences in the first population of DNA.

20. A kit comprising:
the plurality of blocking oligonucleotides of claim 15; and
a strand-displacing polymerase, optionally wherein the strand-displacing polymerase is phi29 polymerase.

* * * * *